(12) United States Patent
Kim et al.

(10) Patent No.: US 8,097,704 B2
(45) Date of Patent: Jan. 17, 2012

(54) ANTIBODY SPECIFICALLY BINDING TO DR5 AND COMPOSITION FOR PREVENTING OR TREATING CANCERS COMPRISING THE SAME

(75) Inventors: Yong Sung Kim, Suwon-si (KR); Myung Hee Kwon, Suwon-si (KR); Seung Hyun Lee, Wonju-si (KR); Kyung Jin Park, Suwon-si (KR); Hae Won Lee, Chuncheon-si (KR)

(73) Assignee: Ajou University Industry-Academic Cooperation Foundation, Suwon-si (KR)

( * ) Notice: Subject to any disclaimer, the term of this patent is extended or adjusted under 35 U.S.C. 154(b) by 256 days.

(21) Appl. No.: 12/307,293

(22) PCT Filed: May 31, 2007

(86) PCT No.: PCT/KR2007/002644
§ 371 (c)(1),
(2), (4) Date: Jan. 2, 2009

(87) PCT Pub. No.: WO2008/004760
PCT Pub. Date: Jan. 10, 2008

(65) Prior Publication Data
US 2009/0317396 A1    Dec. 24, 2009

(30) Foreign Application Priority Data

Jul. 5, 2006 (KR) .......................... 10-2006-0063126
Apr. 20, 2007 (KR) .......................... 10-2007-0038937

(51) Int. Cl.
*C07K 16/00* (2006.01)
(52) U.S. Cl. .................................. 530/387.1; 424/130.1
(58) Field of Classification Search .......................... None
See application file for complete search history.

(56) References Cited

U.S. PATENT DOCUMENTS

2003/0190687 A1    10/2003    Zhou et al.

OTHER PUBLICATIONS

Stedman's Medical Dictionary. 27th ed. Thomas Lathrop Stedman. Baltimore: Lippincott Williams & Wilkins, 2000. pp. 2098.*
Apantaku et al. American Family Physician, 62(3):596-602, 605-6, Aug. 2000).*
Begley DJ, Pharmacol. Therapy, vol. 104(1), pp. 29-45, 2004.*
Misra et al. J. Pharmacy and Pharmaceutical Sciences, vol. 6(2), pp. 252-273, 2003.*
Martin et al (Journal of the National Cancer Institute, vol. 92, No. 14: pp. 1126-1135, Jul. 19, 2000).*

Park, K.-J., et al., "A novel anti-DR5 human scFv antibodies induce cell death in multiple tumors in monomeric form", 2006 Annual Meeting and International Symposium on Systemic Innovation for Microbial Biotechnology, by The Korean Society for Microbiology and Biotechnology, J-13 (Jun. 20, 2006).
Lee, H.-W., et al, "Construction and characterization of a pseudo-immune human antibody library using yeast surface display", Biochemical and Biophysical Research Communications, vol. 346, pp. 896-903 (Jun. 9, 2006).
Yagita, H., et al., "TRAIL and its receptors as targets for cancer therapy", Cancer Science, vol. 96 (10), pp. 777-783 (Oct. 2004).
Ichikawa, K., et al., "Tumoricidal activity of a novel anti-human DR5 monoclonal antibody without hepatocyte cytotoxicity", Nature Medicine, vol. 7(8), pp. 954-960 (Aug. 2001).
Ohtsuka, T., et al., "Synergistic induction of tumor cell apoptosis by death receptor antibody and chemotherapy agent through JNK/p38 and mitochondrial death pathway", Oncogene, vol. 22(13), pp. 2034-2044 (Apr. 3, 2003).
Kyung Jin Park et al., "Systemic Innovation for Microbial Biotechnology". The Korean Society for Microbiology and Biotechnology, J-13 (2006).
Hae-Won Lee et al., "Construction and characterization of a pseudo-immune human antibody library using yeast surface display". Biochemical and Biophysical Research Communications, 346: 896-903 (2006).
Hideo Yagita et al., "TRAIL and its receptors as targets for cancer therapy" Cancer Sci., 95(10): 777-783 (2004).
Kimihisa Ichikawa et al., "Tumoricidal activity of a novel anti-human DR5 monoclonal antibody without hepatocyte cytotoxicity" Nature Medicine, 7(8): 954-960 (2001).
Toshiaki Ohtsuka et al., "Synergistic induction of tumor cell apoptosis by death receptor antibody and chemotherapy agent through JNK/p38 and mitochondrial death pathway" Oncogene, 22: 2034-2044 (2003).

* cited by examiner

*Primary Examiner* — Laura B Goddard
*Assistant Examiner* — Meera Natarajan
(74) *Attorney, Agent, or Firm* — Sughrue Mion, PLLC

(57) ABSTRACT

The present invention provides an antibody specifically binding to death receptor 5 (DR5), which is selected from the group consisting of: an antibody comprising a heavy chain variable region ($V_H$) having the amino acid sequences of SEQ ID NOs: 1 to 3 at complementary determining regions (CDRs) and a light chain variable region ($V_L$) having the amino acid sequences of SEQ ID NOs: 4 to 6 at CDRs; and an antibody comprising a ($V_H$) having the amino acid sequences of SEQ ID NOs: 7 to 9 at CDRs and a ($V_L$) having the amino acid sequences of SEQ ID NOs: 10 to 12 at CDRs, and a composition for preventing or treating a cancer comprising the same. The antibody of the present invention can be effectively used for the prevention or treatment of various cancers, through inducing autophagic cell death of TRAIL-sensitive cancer cells as well as TRAIL-resistant cancer cells by specific binding to DR5.

10 Claims, 33 Drawing Sheets
(4 of 33 Drawing Sheet(s) Filed in Color)

Fig. 1A

```
        Q  V  Q  L  Q  Q  S  G  P  G  L  V  K  P  S  Q  T  L  S  L
  1     caggtacagctgcagcagtcaggtccaggactggtgaagccctcgcagaccctctcactc    60
        T  C  A  I  S  G  D  S  V  S  S  T  T  V  A  W  D  W  I  R
 61     acctgtgccatctccggggacagtgtctctagcaccactgttgcctgggactggatcagg   120
        Q  S  P  S  R  G  L  E  W  L  G  R  T  Y  Y  R  S  K  W  Y
121     cagtccccatcgagaggccttgagtggctgggaaggacatattataggtcgaagtggtat   180
        N  E  Y  A  V  S  V  K  S  R  I  T  I  N  V  D  T  S  K  N
181     aatgaatatgcagtatctgtgaaaagtcgaataaccatcaatgtagacacatccaagaac   240
        Q  I  S  L  Q  L  N  S  V  T  P  E  D  T  A  V  Y  Y  C  A
241     cagatctccctgcagctgaactctgtgactccgaggacacggccgtctattactgtgca   300
        R  P  D  A  G  R  G  A  F  D  I  W  G  Q  G  T  T  V  T
301     agagagccagatgccggcaggggggcttttgatatctggggccaagggaccacggtcacc   360
        S  P  L  R  W  G  R  F  G  W  R  G  L  G  R  G  W  L  R  S
361     tctcctctgaggtggggcggttcgggtggcgggggctcgggcggggggtggctcagatct   420
        P  V  T  Q  S  P  G  T  L  S  L  S  P  G  E  R  A  T  L  S
421     ccagttacccagtctccaggcaccctgtctttgtctccaggggaagagccaccctctcc   480
        C  R  A  S  Q  S  V  S  S  S  H  L  A  W  Y  Q  Q  K  P  G
481     tgcagggccagtcagagtgttagcagcagccacttagcctggtaccagcagaaacctggc   540
        Q  A  P  R  L  L  I  Y  G  A  S  S  R  A  T  G  I  P  D  R
541     caggctcccaggctcctcatctatggtgcatccagcagggccactggcatcccagacagg   600
        F  S  G  S  G  S  G  T  D  F  T  L  T  I  S  S  L  E  P  E
601     ttcagtggcagtgggtctgggacagacttcactctcaccatcagcagcctagagcctgaa   660
        D  F  A  V  Y  Y  C  Q  Q  R  S  N  W  P  P  R  A  Y  F  G
661     gattttgcagtttattactgtcagcagcgtagcaactggcctccgcgggcggtcttcggc   720
        Q  G  T  R  L  E  I  K
721     caagggacacgactggagattaaa   744
```

Fig. 1B

```
      Q  V  Q  L  Q  Q  S  G  P  G  R  V  Q  P  S  Q  T  L  S  L
  1 caggtacagctgcagcagtcaggtccaggacgggtgcagcctcgcagccctctcactc 60
      T  C  A  I  S  G  D  S  V  S  N  N  N  A  A  W  Y  W  I  R
 61 acctgtgccatctccggggacagtgtctctaacaacaatgctgcttggtactggatcagg 120
      Q  S  P  S  R  G  L  E  W  L  G  R  T  Y  Y  R  S  K  W  Y
121 cagtccccatcgagaggccttgagtggctgggaaggacatactacaggtccaagtggtat 180
      N  D  Y  A  V  S  V  K  S  R  I  T  I  S  P  D  T  S  K  N
181 aatgattatgcagtatctgtgaaaagtcgaataaccatcagcccagacacgtccaagaac 240
      Q  F  S  L  Q  L  N  S  V  T  P  E  D  T  A  V  Y  Y  C  A
241 cagttctccctgcagttgaactctgtgactccgaggacacggctgtgtattactgtgca 300
      R  R  G  D  G  N  S  Y  F  D  Y  W  G  Q  G  T  L  V  T  V
301 agaagaggagatgggaactcctactttgactactggggccagggaaccctggtcaccgtc 360
      S  S  G  I  L  R  W  G  R  F  G  W  R  G  L  G  R  G  W  L
361 tcctcaggaattctaaggtgggggcggttcgggtggcgggggctcgggcggggtggctc 420
      E  I  V  L  T  Q  S  P  G  T  L  S  L  S  P  G  E  R  A  T
421 gaaattgtattgacacagtctccaggcaccctgtctttgtctccaggggaaagagccacc 480
      L  S  C  R  A  S  Q  S  V  S  S  G  Y  V  S  W  Y  R  Q  K
481 ctctcctgcagggccagtcagagtgttagcagcggctacgtatcctggtaccggcagaaa 540
      P  G  Q  A  P  R  L  L  I  Y  G  A  S  T  R  A  T  G  I  P
541 cctggccaggctccccggctcctcatctatggtgcatccaccagggccactggcatccca 600
      D  R  F  S  G  S  G  S  G  T  D  F  T  L  T  I  S  R  L  E
601 gacaggttcagtggcagtgggtctgggacagacttcactctcaccatcagcagactggag 660
      P  E  D  F  A  V  Y  Y  C  H  Q  Y  G  S  S  P  N  T  Y  G
661 cctgaagattttgcagtgtattactgtcaccagtatggtagctcacccaacacttatggc 720
      Q  G  T  K  V  G  I  K
721 caggggaccaaggtggggatcaaa 744
```

Fig. 15
  
Control  HW1  HW6

US 8,097,704 B2

ANTIBODY SPECIFICALLY BINDING TO DR5 AND COMPOSITION FOR PREVENTING OR TREATING CANCERS COMPRISING THE SAME

FIELD OF THE INVENTION

The present invention relates to an antibody specifically binding to death receptor 5 (DR5), and a composition for preventing or treating cancers comprising the same.

BACKGROUND OF THE INVENTION

Among the apoptotic pathways involving p53-independent tumor necrosis factor receptors (TNFRs), cell death through the death receptor 5 (DR5, TRAIL receptor 2, TRICK2) or the death receptor 4 (DR4, TRAIL receptor 1) pathway activated by TNF-related apoptosis inducing ligand (TRAIL) has been a very attractive target for cancer therapy as they can specifically induce cancer cell death with little adverse side effects on normal cells (Ashkenazi et al., *J. Clin. Invest.*, 104:155-162, 1999; and Ashkenazi, *Nat. Rev. Cancer*, 2:420-430, 2002).

Currently, there exist several methods to develop caner cell-specific therapeutic agents which target DR4 or DR5 such as a method using a recombinant TRAIL (for example, $114^{th}$ to $281^{st}$ amino acid residues of TRAIL) as a ligand of the death receptor and a method of developing an agonistic antibody among mouse- or human-derived complete antibodies (e.g.: mAb or IgG) specific to the death receptor (Pollack et al., *Clin. Cancer Res.*, 7:1362-1369, 2001; Jo et al., *Nat. Med.*, 6:564-567, 2000; Ichikawa et al., *Nat. Med.*, 7:954-960, 2001; and Walczak et al., *Nat. Med.*, 5:157-161, 1999). However, the recombinant TRAIL is very unstable and tends to form a soluble oligomer, whose apoptotic activity is about 20 to 100 times lower, and it causes side effects such as cytotoxicity and immune reaction on normal cells such as astrocytes, hepatocytes and keratinocytes (Jo et al., *Nat. Med.*, 6:564-567, 2000). Further, TRAIL is not capable of inducing more than 50% cell death of malignant tumor cells (Zhang et al., *Cancer Gene Ther.*, 12:228-237, 2005). Hence, a cancer cell that can be killed by TRAIL is designated a TRAIL-sensitive cancer cell, and a cancer cell not killed by TRAIL, a TRAIL-resistant cancer cell.

There have been developed antibodies, which have the specific binding affinity to DR5 to induce the cell death: humanized antibodies developed from mouse-derived monoclonal antibodies such as TRA-8 (mouse IgG) (Walczak et al, *Nat. Med.*, 5:157-161) and AD5-10 (mouse IgG) (Guo et al., *J. Biol. Chem.*, 280:41940-41952, 2005), as well as human-derived monoclonal antibodies such as HGS-ETR2 (human IgG1) (Georgakis et al., *Br. J. Haematol.*, 130:501-510, 2005) and KMTR2 (human IgG4) (Motoki et al., *Clin. Cancer Res.*, 11:3126-3135, 2005).

However, the above antibodies induce apoptotic cell death of TRAIL-sensitive cancer cells but not TRAIL-resistant cancer cells. Further, the antibodies in the form of an antigen-binding fragment (Fab) or a single chain variable fragment (scFv) having a monovalent antigen binding site does not induce cell death of cancer cells (e.g.: KMTR2), while antibodies in the form of IgG having divalent antigen binding site (e.g.: HGS-ETR2 and AD5-10) show cytotoxicity or induced cell death when an IgG is used as a cross-linker (Chuntharapai et al., *J. Immunol.*, 166:4891-4898, 2001; Motoki et al., *Clin. Cancer Res.*, 11:3126-3135, 2005; and Wajant et al., *Oncogene*, 20:4101-4106, 2001). But, it has not been reported that an anti-DR5 antibody in the form of a scFv and a Fab induces cancer cell death.

Currently, there remains a question as to whether or not autophagy is the mechanism responsible for inducing cancer cell death (Kondo et al., *Nat. Rev. Cancer*, 5:726-734, 2005), and it has been reported that only specific compounds can kill cancer cells by an autophagic cell death pathway (Yu et al., *Science*, 304:1500-1502, 2004). However, there have been no reports of anti-DR5 mAbs which induce autophagic cell death.

SUMMARY OF THE INVENTION

Accordingly, it is an object of the present invention to provide an antibody inducing autophagic cell death of both TRAIL-sensitive and TRAIL-resistant cancer cells through specifically binding to DR5.

It is another object of the present invention to provide a DNA encoding the antibody.

It is a further object of the present invention to provide a cell transformed with the DNA or an expression vector comprising the DNA.

It is a still further object of the present invention to provide a composition for preventing or treating cancers comprising the antibody.

It is a still further object of the present invention to provide a method of preventing or treating cancers by using the antibody.

In accordance with one aspect of the present invention, there is provided an antibody specifically binding to death receptor 5 (DR5), which is selected from the group consisting of: an antibody comprising a heavy chain variable region ($V_H$) having the amino acid sequences of SEQ ID NOs: 1 to 3 at complementary determining regions (CDRs) and a light chain variable region ($V_L$) having the amino acid sequences of SEQ ID NOs: 4 to 6 at CDRs; and an antibody comprising a $V_H$ having the amino acid sequences of SEQ ID NOs: 7 to 9 at CDRs and a $V_L$ having the amino acid sequences of SEQ ID NOs: 10 to 12 at CDRs.

In accordance with another aspect of the present invention, there is provided a DNA encoding the antibody.

In accordance with a further aspect of the present invention, there is provided a cell transformed with the DNA or an expression vector comprising the DNA.

In accordance with a still further aspect of the present invention, there is provided a composition for preventing or treating a cancer comprising the antibody as an active ingredient.

In accordance with a still further aspect of the present invention, there is provided a method of preventing or treating a cancer comprising administering the antibody to a subject.

BRIEF DESCRIPTION OF DRAWINGS

The patent or application file contains at least one drawing executed in color. Copies of this patent or patent application publication with color drawing(s) will be provided by the Office upon request and payment of the necessary fee.

The above and other objects and features of the present invention will become apparent from the following description of the invention taken in conjunction with the following accompanying drawings, which respectively show:

FIGS. 1A and 1B: amino acid sequences of HW1 and HW6, and DNAs encoding thereof as anti-DR5 scFv antibodies specifically binding to DR5, respectively (wherein, CDR1 to CDR3 of a heavy chain variable region, a linker oligopeptide and CDR1 to CDR3 of a light chain variable region of each antibody are underlined in order);

FIG. 15: microscopic images showing that no cytotoxicity to normal human brain astrocytes was caused by HW1 or HW6;

DETAILED DESCRIPTION OF THE INVENTION

Figure 2:
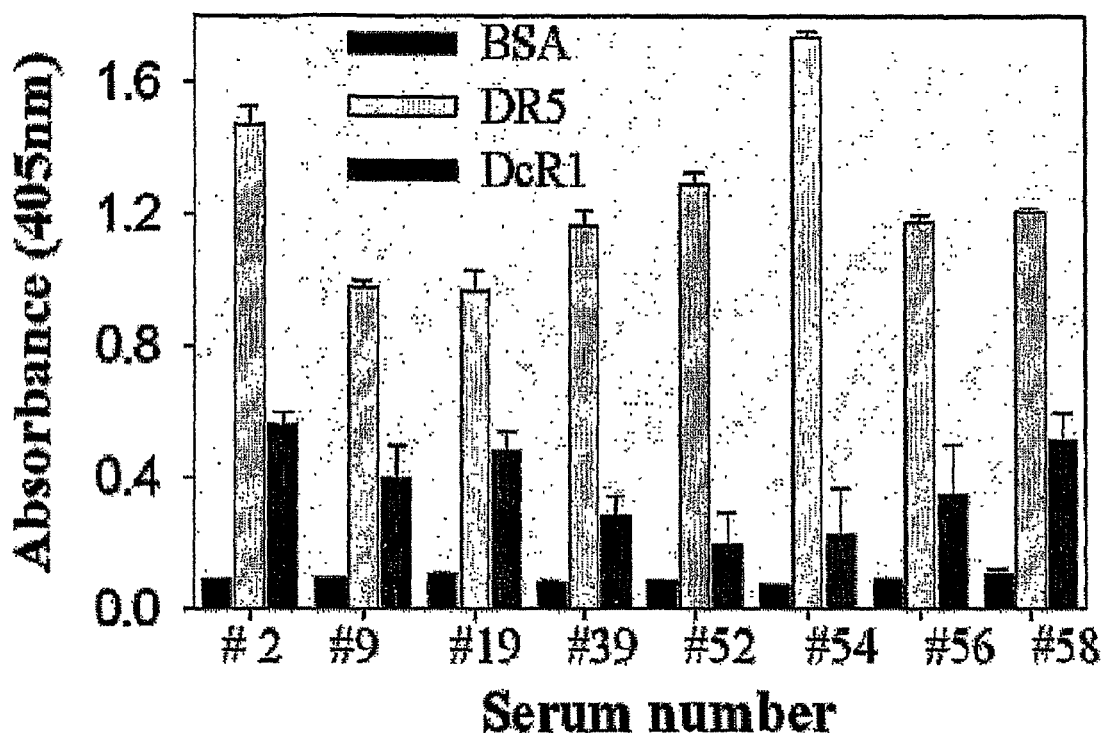
FIG. 2: the result of ELISA quantifying the antibody titer against DR5, DcR1 and BSA in 8 serums showing high antibody titers against DR5.

In the present invention, the term "death receptor 5 (DR5) protein" means a receptor as a member of tumor necrosis factor (TNF) receptor family, which binds to TRAIL and has a C-terminal cytoplasmic death domain (Pan et al., *Science*, 277:815-818, 1997). When DR5 binds to TRAIL, apoptosis is induced in TRAIL-sensitive cancer cells, but not in normal cells.

In the present invention, the term "DR5" includes any protein having the above characteristics, e.g., a protein having the amino acid sequences described in U.S. Pat. No. 6,872,568.

In the present invention, the term "antibody" may be a whole antibody or a fragment thereof. The whole antibody can be a monomer selected from the group consisting of IgG, IgM, IgA, IgD and IgE, or a multimer formed by combining monomers. Further, the term "a functional fragment of an antibody" means an antibody having heavy chain and light chain variable regions of a whole antibody actually recognizing the same epitope recognized by the whole antibody. The functional fragment of an antibody may be a single chain variable fragment (scFv), (scFv)$_2$, Fab, Fab', F(ab')$_2$ or scFv-Fc, and it is preferably scFv.

Further, in the present invention, the term "single chain variable fragment (scFv)" means an antibody fragment of a single chain polypeptide form having a heavy chain variable region and a light chain variable region linked through a linker peptide.

The antibody may be produced by any of the conventional methods known to those in the art, such as the phage display method or yeast cell surface expression system.

scFv may be prepared by any of the conventional methods known to those in the art, e.g., the method described in U.S. Pat. No. 4,946,778 or 5,258,498, and Fab, Fab' and F(ab')$_2$ fragments may be prepared by recombinant antibody technology, e.g., the method described in International Patent Publication No. WO 92/22324.

The inventive antibody may be derived from any animal which may be mammals excluding human, birds and so on. Preferably, the antibody may be derived from a human, mouse, donkey, sheep, rabbit, goat, guinea pig, camel, horse or chicken. The antibody derived from a human is an antibody having amino acid sequences of human immunoglobulin, and may include an antibody isolated from human immunoglobulin libraries, or an antibody isolated from animals, which are transformed to produce one or more human immunoglobulins and incapable of expressing endogenous immunoglobulin (see U.S. Pat. No. 5,939,598)

The inventive antibody may be conjugated with a marker including, but not limited to, an enzyme, fluorescent material, radioactive material, protein and so on. The methods to conjugate the materials are well known in the art.

The inventive antibody specifically binds to DR5 protein. In the present invention, the term "specifically bind" means that the inventive antibody does not bind to DR5-like TNFR family receptors such as DcR1 (death decoy receptor 1), DcR2, DR4, TNFR1, TNFR2 and CD95.

In the inventive antibody, the amino acid sequences of SEQ ID NOs: 1 to 3 or 7 to 9 are CDR1, CDR2 and CDR3, respectively, of the heavy chain variable region of an antibody specifically binding to DR5, while the amino acid sequences of SEQ ID NOs: 4 to 6 or 10 to 12 are CDR1, CDR2 and CDR3, respectively, of the light chain variable region of an antibody specifically binding to DR5.

Preferable examples of the inventive antibody are scFv antibodies, HW1 and HW6, which have the amino acid sequences of SEQ ID NOs: 13 and 14, respectively, and the antibodies comprise CDR1 to CDR3 of a heavy chain variable region, linker-oligopeptide and CDR1 to CDR3 of a light chain variable region in order (see FIGS. 1A and 1B).

HW1 and HW6 specifically bind to DR5, and have binding affinities ($K_D$) of about $2.02 \times 10^{-7}$ M, and $5.45 \times 10^{-8}$ M, respectively. Further, the antibodies in the form of monovalent scFv induce autophagic cell death of both TRAIL-sensitive and -resistant cancer cells in the absence of a cross linker, but they are not toxic to normal cells.

Accordingly, the inventive antibody is believed to induce autophagic cell death of various cancer cells including TRAIL-resistant cancer cells through specific binding to epitopes (binding sites) of DR5 which do not overlap with the TRAIL-binding epitopes.

The present invention further provides a DNA encoding the inventive antibody.

The DNA is preferably a DNA encoding the scFv having the amino acid sequence of SEQ ID NO: 13 or 14, and more preferably, a DNA having the nucleotide sequence of SEQ ID NO: 15 or 16.

The DNA sequence encoding the inventive antibody can be obtained by any of the conventional methods known in the art. For example, based on the DNA sequence encoding the antibody heavy or light chain, a part thereof, or the corresponding amino acid sequence, an appropriate DNA sequence can be synthesized by the well known oligonucleotide synthesis method, e.g., site-directed mutagenesis and polymerase chain reaction (PCR).

Further, the present invention provides a cell transformed with the inventive DNA or an expression vector comprising the DNA.

The inventive DNA or the expression vector comprising the DNA may be transferred to a host cell by any of the conventional methods, e.g., viral transfection or non-viral method. Such introduction of the DNA or the expression vector may be conducted in accordance with any of the methods known to those in the art including adenoviral transformation, gene gun, liposome-mediated transformation, retrovirus or lentivirus-mediated transformation, plasmid or adeno-associated virus. Further, the transformed cell may be transplanted together with carriers having gene delivery system, which can release or deliver the designed gene to the cells of a subject for a long period of time.

The present invention further provides a method of producing the inventive antibody molecule comprising the steps of: 1) expressing the antibody by culturing a host cell comprising the inventive DNA sequence or an expression vector comprising the DNA under a suitable condition; and 2) isolating the expressed antibody.

The antibody molecule may be accumulated in the cell cytoplasm, or in the periplasm or extracellular medium (supernatant) using a proper signal sequence, and the accumulation thereof in the periplasm or extracellular medium is preferred. Further, the produced antibody molecule may be refolded to confer a functional conformation thereto using any of the conventional methods known in the art.

In order to produce only a heavy chain or a light chain polypeptide of the antibody molecule, a single vector comprising a heavy chain or light chain polypeptide may be transformed into a host cell. In order to produce both heavy chain and light chain polypeptides of the antibody molecule, both the first vector encoding a light chain polypeptide and the second vector encoding a heavy chain polypeptide, or a single vector comprising both heavy chain and light chain polypeptides may be transformed into a host cell.

As described above, the inventive antibody, which induces autophagic cell death of DR5-expressed TRAIL-sensitive and TRAIL-resistant cancer cells by specific binding to DR5, can be used to prevent or treat various cancers. Such cancers may be any cancer expressing DR5 and include TRAIL-sensitive and TRAIL-resistant cancers, such as breast cancer, colon cancer, brain tumor, glioma, ovarian cancer, endometrial cancer, bone sarcoma, cervix cancer, prostatic cancer, lung cancer, synovial cancer, pancreatic cancer and sarcoma.

Accordingly, the present invention further provides a composition for preventing or treating cancer comprising the inventive antibody as an active ingredient.

The inventive composition for preventing or treating cancer may additionally comprise one or more pharmaceutically acceptable excipients, carriers, diluents and so on.

Example of the carrier employed in the present invention is a slowly metabolized macromolecule such as protein, polypeptide, liposome, polysaccharide, polylactic acid, polyglycolic acid, polymeric amino acid, amino acid polymer and inactive viral particle. For example, a pharmaceutically acceptable salt, such as a salt of inorganic acid (e.g., hydrochloride, hydrobromide, phosphate and sulfate), and a salt of organic acid (e.g., acetate, propionate, malonate and benzoate); a liquid such as water, saline solution, glycerol and ethanol; and an auxiliary material such as a wetting agent, an emulsifier and a pH buffer may be used.

The pharmaceutically acceptable carrier is described in [Remington's Pharmaceutical Sciences, Mack Publishing Company, 1991].

Further, the composition may be formulated to a unit dosage form suitable for administering to a patient, preferably for administering a protein drug, by conventional methods in the pharmaceutical field, and it can be administered in accordance with any conventional method in the art through oral route or parenteral route such as intravenous, intramuscular, intraarterial, intramedullar, intrathecal, intraventricular, intrapulmonary, intracutaneous, subcutaneous, intraperitoneal, intranasal, enteral, topical, sublingual, intravaginal or intrarectal route without limitation.

Example of the formulations suitable for such purposes may include oral formulations such as tablet, pill, dragee, powder, capsule, syrup, solution, gel, suspension, emulsion and microemulsion; and parenteral formulations such as injection formulation (e.g., injection ampule), infusion formulation, and spray formulation (e.g., hypospray). Injection formulation or infusion formulation may be in the form of suspension, solution or emulsion, and include formulation aids such as suspending agents, preservatives, stabilizers and/or dispersing agents. Further, the antibody molecule may be formulated in the form of a dried formulation, which can be readjusted to a suitable sterile solution before use.

Because the composition of the present invention comprises an antibody molecule easily degraded in the gastrointestine, the composition for gastrointestinal administration is preferred to include an agent, which protects the antibody from degradation and is absorbed into the gastrointestine after releasing the antibody.

The present invention further provides a method of preventing or treating a cancer comprising a step of administering the inventive antibody to an animal, preferably a mammal, more preferably a human, in accordance with any methods described above.

In the inventive method of preventing or treating a cancer, the composition or pharmaceutical formulation may be used solely or in combination with other anticancer agents, for instance, TRAIL or an anticancer agent conventionally used in the art.

Further, the inventive antibody may be administered by gene therapy. For this purpose, DNAs encoding heavy and light chains of the inventive antibody or an expression vector thereof should be introduced into a patient by any of the conventional methods known in the art so that the heavy and light chains are combined in situ to form the antibody molecule.

The inventive antibody as an active ingredient of the inventive composition or pharmaceutical formulation may be administered in a dose ranging from about 0.01 to 50 mg/kg (body weight), preferably 0.1 to 20 mg/kg (body weight) per day in case of a mammal including a human being. The inventive composition or pharmaceutical composition may be administered in a single dose or in divided doses. However, it should be understood that the amount of the active ingredient actually administered ought to be determined in light of various relevant factors including the disease to be treated, the condition to be treated, the severity of the patient's symptom, the chosen route of administration, and the body weight, age and sex of the individual patient, drug combination, reaction sensitivity, and tolerance/reactivity to treatment; and, therefore, the above dose should not be intended to limit the scope of the invention in any way.

The following Examples are intended to further illustrate the present invention without limiting its scope.

EXAMPLE 1

Selection of a Serum Having a High Antibody Titer Against Dr5

In order to construct human antibody libraries using a serum having a high antibody titer against death receptor DR5 and death decoy receptor 1 (DcR1), antibody titers against DR5 and DcR1 of blood serums of 60 normal persons were measured by ELISA. At this time, bovine serum albumin (BSA) was used as a control antigen.

Specifically, each well of a 96-well ELISA plate (Nunc, Invitrogen) was coated with 10 µg/ml of a test antigen dissolved in TBS (50 mM Tris-HCl, pH 7.5, 50 mM NaCl) at 25° C. for 1 hour, washed with TBS containing 0.05% tween 20 (TBST) 3 times, and blocked with TBS containing 3% BSA. Each diluted serum sample (1:100) was added to each well and incubated at 25° C. for about 1 hour, and the well was washed with TBST. 100 µl of alkaline phosphatase-conjugated anti-human IgG/IgA (2.5 µg/ml, Pierce) was added to each well, incubated at 25° C. for about 1 hour, and washed with TBST. Then, 100 µl of p-NPP (p-nitrophenyl phosphate, 1 mg/ml) was added to each well, allowed to react for 4 hours, and the absorbance was read at 405 nm with a microplate reader to quantify the antibody titer against DR5 or DcR1 antigen. The results for 8 serums having high antibody titers against DR5 and DcR1 antigen are shown in FIG. 2.

As shown in FIG. 2, the selected 8 serums each showed antibody titers against DR5 and DcR1 which are more than 2 times higher than that of BSA as a control.

EXAMPLE 2

Construction of a scFv Antibody Library (2-1) Amplification of a Heavy Chain and a Light Chain of the Antibody Total RNA was extracted from peripheral blood lymphocytes of the selected 8 blood samples of Example 1 using TRIzol reagent (Invitrogen, USA), and mRNA was separated by using oligotex mRNA kit (Qiagen). Then, single strand cDNA libraries of a human scFv antibody were amplified by reverse transcription with random hexamers as primers (Amersham Pharmacia Biosciences) using AccuPower RT Pre-Mix (Bioneer, Korea).

In order to amplify the heavy chain variable region ($V_H$) of human antibody IgG (γ) and IgM (µ), and the light chain variable region ($V_\kappa$ and $V_\lambda$) of human antibody, a total of 71 PCRs (28, 16 and 27 reactions for $V_H$, $V_\kappa$ and $V_\lambda$, respectively) were performed using each primer set. Each PCR condition was 30 cycles of 2 min at 95° C., 1 min at 55° C. and 1 min at 72° C.

The primers used were those of Little et al. (*J. Immunol. Methods,* 231:3-9, 1999) with the following slight modifications.

Specifically, in order to generate a linker sequence between $V_H$ and $V_L$ gene, the sequence 5'-CGA GCC CCC GCC ACC CGA ACC GCC CCC ACC TCT-3' (SEQ ID NO: 17) was added to the 5' end of the reverse primer of $V_H$ and the sequence 5'-GGT TCG GGT GGC GGG GGC TCG GGC GGG GGT GGC TCA GAT CT-3' (SEQ ID NO: 18) was added to the 5' end of the forward primers of $V_\kappa$ and $V_\lambda$.

Further, in order to allow transforming the amplified scFv libraries into the yeast surface display vector by homologous recombination, the sequence 5'-AGT GGT GGT GGT GGT TCT GGT GGT GGT GGT TCT GGT GGT GGT GGT TCT GCT AGC-3' (SEQ ID NO: 19) was added to the 5' end of the forward primer of $V_H$ and the sequence 5'-TCA GAT CTC GAG CTA TTA CAA GTC CTC TTC AGA AAT AAG CTT TTG TTC GGA TCC-3' (SEQ ID NO: 20) was added to the 5' end of the reverse primers of $V_\kappa$ and $V_\lambda$.

(2-2) Amplification of a scFv Antibody Gene

The amplified $V_H$ and $V_L$ genes were subjected to 1% agarose gel electrophoresis and purified. Equal amounts of the purified $V_H$ and $V_L$ genes were mixed together, and overlap extension PCR was conducted to prepare scFv gene repertoires. The PCR products were purified as described above. Each PCR condition was 30 cycles of 2 min at 95° C., 1 min at 55° C. and 1 min at 72° C.

(2-3) Construction of a scFv Antibody Gene Library

10 µg/µl of the obtained scFv antibody gene libraries were mixed with 1 µg/µl of a scFv yeast surface display vector (PCTCON; Colby et al., *Methods Enzymol.,* 388:348-358, 2004), and the mixture was transformed into a yeast EBY 100 strain (Invitrogen) by electrophoration. The transformants were pooled and propagated directly in liquid selective SD-CAA medium (-ura, -trp), which contained 20 g/l glucose, 6.7 g/l yeast nitrogen base without amino acids (Difco, USA), 5.4 g/l $Na_2HPO_4$, 8.6 g/l $Na_2HPO_4 \cdot H_2O$ and 5 g/l casamino acid, and then the libraries which induced cell surface expression of scFv were selected using a selective SG-CAA medium, which contained the same composition as SD-CAA, except that glucose was replaced with galactose. The cells containing the libraries were each serially diluted 10-fold with the selective SD-CAA medium, and the library size was determined by plating each diluted cells on the selective SD-CAA agar plate.

As a result, approximately 2×10⁶ scFv antibody libraries, so called a pseudo-immune library, were constructed.

EXAMPLE 3

Selection of an Anti-DR5 scFv Antibody Library

Figure 3:
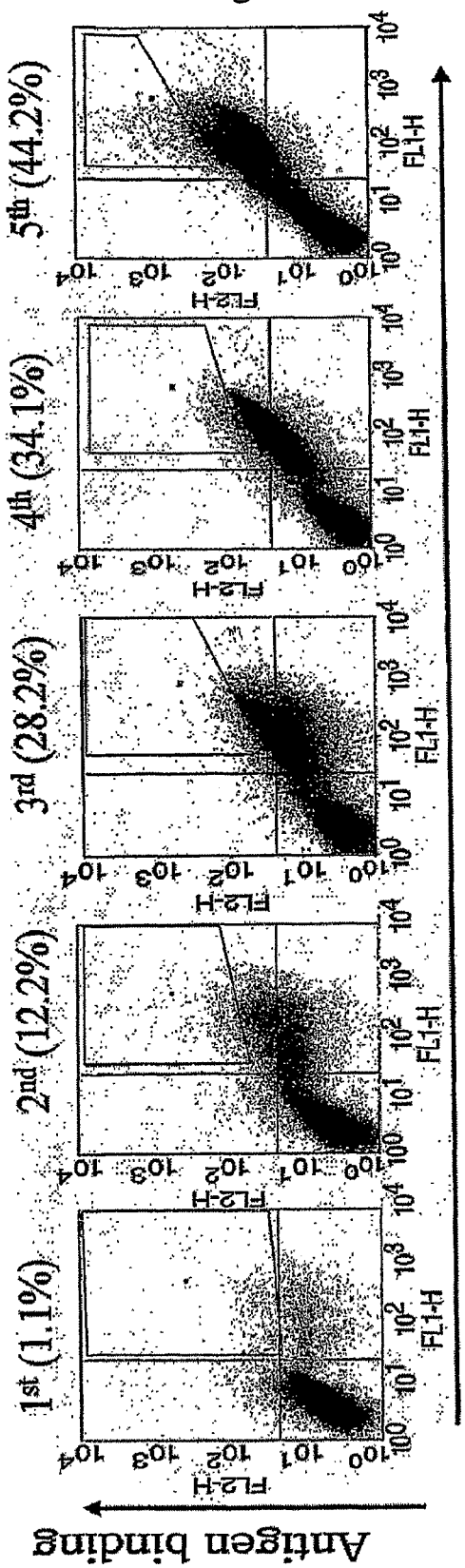
FIG. 3: the result of FACS (fluorescence activated cell sorting) isolating an anti-DR5 scFv antibody library expressed on cell surface by using biotin-labeled DR5 as an antigen.

In order to select scFv antibodies having high specific affinity to DR5 among the scFv antibody libraries obtained in Example 2, the cells containing the selected libraries were incubated with anti-c-myc 9E10 mAb (1:100 dilution, Ig Therapy) and 1 µM of biotin-labeled DR5 by EZ-LINK™ Sulfo-NHS-LC-Biotinylation kit (Pierce, USA) at 25° C. for 30 min in 0.2 ml of PBSB (phosphate-buffered saline, pH 7.4, containing 1 mg/ml of BSA). The cells were washed with ice-cold PBSB, and labeled with FITC-labeled anti-mouse IgG (1:25 dilution) and streptavidin-R-phycoerythrin conjugate (SA-PE, 1:100 dilution; Molecular Probes, USA) as a secondary antibody, respectively. The labeled cells were washed, resuspended in PBSB, and then one round of MACS (magnetic activated cell sorting) was performed using biotin-labeled DR5 to float the scFv library having the binding affinity to DR5, followed by performing FACS (fluorescence activated cell sorting) to select HW1 and HW6 bound to the antigen in the anti-DR5 scFv antibody libraries expressed on yeast cell surface. The results are shown in FIG. 3.

The nucleotide sequences of the selected HW1 and HW6 were analyzed using a forward primer 5'-GTT CCA GAC TAC GCT CTG CAG G-3' (SEQ ID NO: 21) and a reverse primer 5'-GAT TTT GTT ACA TCT ACA CTG TTG-3' (SEQ ID NO: 22). The amino acid sequences thereof were then deduced from the analyzed nucleotide sequences.

EXAMPLE 4

Anti-DR5 scFv Antibody Expression and Purification

Figure 4:
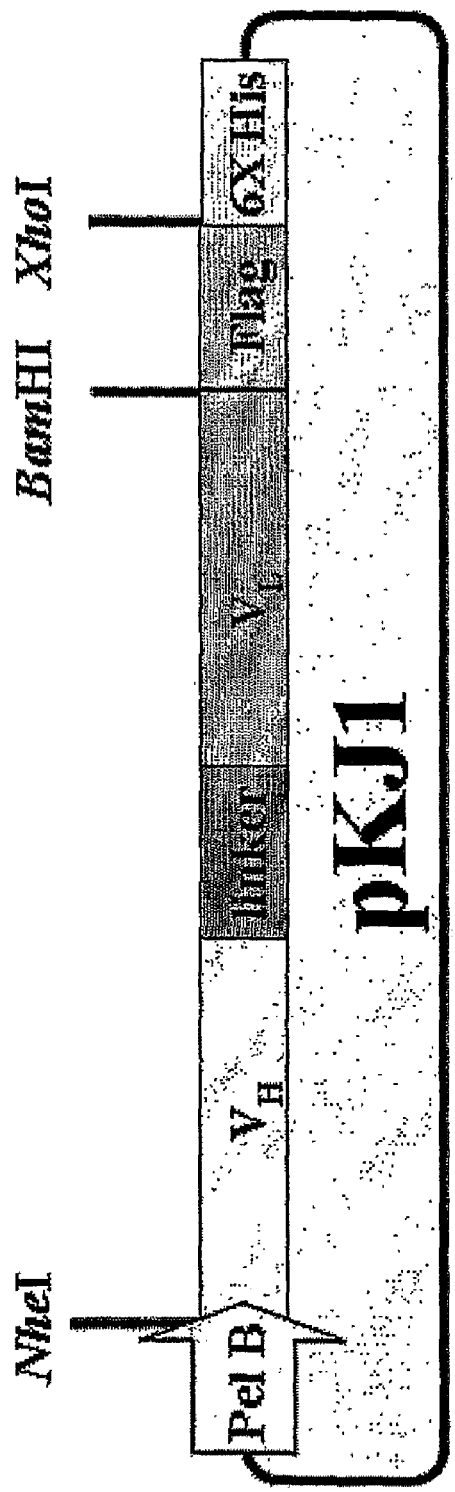
FIG. 4: a diagram of an *E. coli* expression vector prepared by cloning HW1 and HW6 to pKJ1 vector, respectively.

The isolated antibodies HW1 and HW6 of Example 3 were subcloned in-frame into a bacterial expression vector using restriction enzymes NheI and BamHI. The bacterial expression vector was expression vector pKJ1 designed to encode T7 promoter-PelB periplasm targeting sequence-human scFv-Flag tag-6×His tag (FIG. 4). This vector was prepared by inserting PelB nucleotide sequence and restriction enzyme site NheI/BamHI based on pET21b vector (Novagen) and fusing Flag tag and 6×His tag on the C-terminus.

Figure 5A:
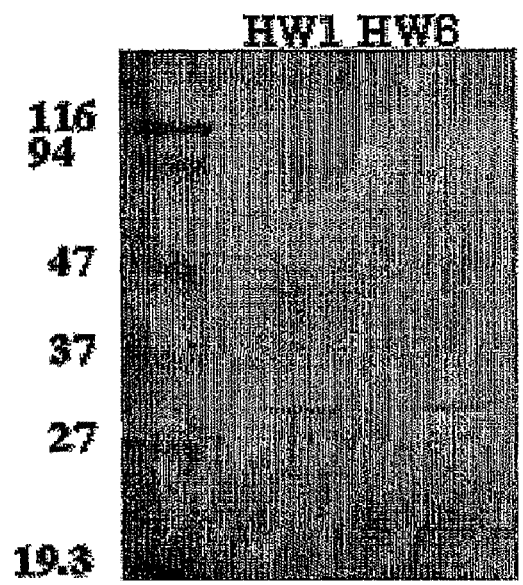
FIGS. 5A and 5B: the results of SDS-PAGE and western blotting, respectively, obtained for HW1 and HW6 expressed in *E. coli* and purified.
Figure 5B:
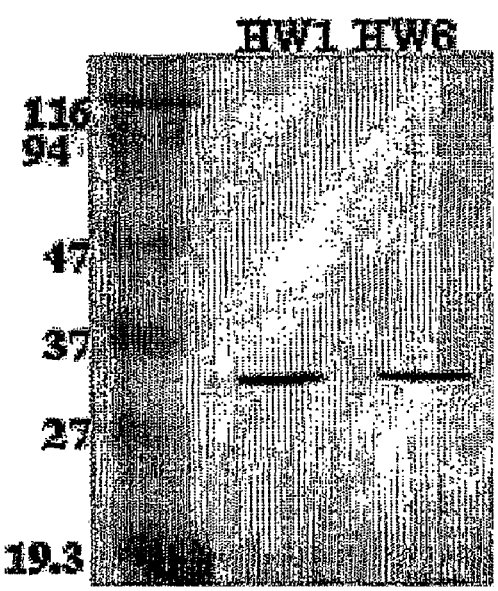

The expression vector was transformed into *E. coli* BL21 (DE3) (Novagen), and the transformed cells were cultured at 37° C. until the OD at 600 nm reached 0.6 to 0.8, followed by induction with 0.5 mM IPTG at 25° C. for 20 hours. The periplasm fraction or supernatant of the cultured bacteria was subjected to Talon resin (Clontech) to purify the expressed antibody, and the size and the purity of the purified antibody were analyzed by SDS-PAGE and western blotting using anti-His tag, respectively. As a result, the antibodies each having size of about 29 kDa (FIG. 5A), and a purity of more than 98% were obtained (FIG. 5B).

TEST EXAMPLE 1

Confirmation of Anti-DR5 scFv Antibody Form

In order to identify whether the HW1 and HW6 purified in Example 4 were in the monomeric or oligomeric form in solution, size exclusion HPLC (SEC), reducing SDS-PAGE and non-reducing SDS-PAGE were performed, respectively.

SEC was performed using PBS (50 mM phosphate, pH 7.4, 150 mM NaCl) as a elution buffer, Sephadex 25 size exclusion column (Pharmacia) and Agilent 1100 HPLC system at a flow rate of 0.7 ml/min, and the absorbance was read at 280 nm. The results are shown in FIG. 6.

Figure 7A:
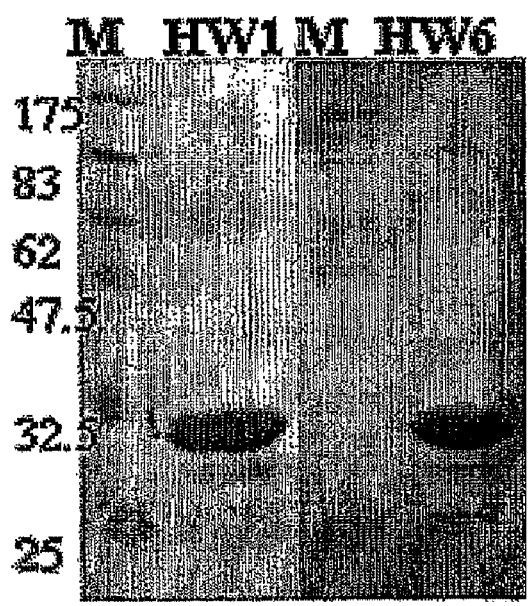
FIGS. 7A and 7B: the results of reducing SDS-PAGE and non-reducing SDS-PAGE of purified HW1 and HW6.

Reducing SDS-PAGE was performed using 10% gel in sample buffer supplemented with 1 mM DTT, and non-reducing SDS-PAGE was performed using 10% gel in sample buffer without 1 mM DTT (see Laemmli UK, *Nature*, 227: 680-685, 1970). The results are shown in FIG. 7.

Figure 6:
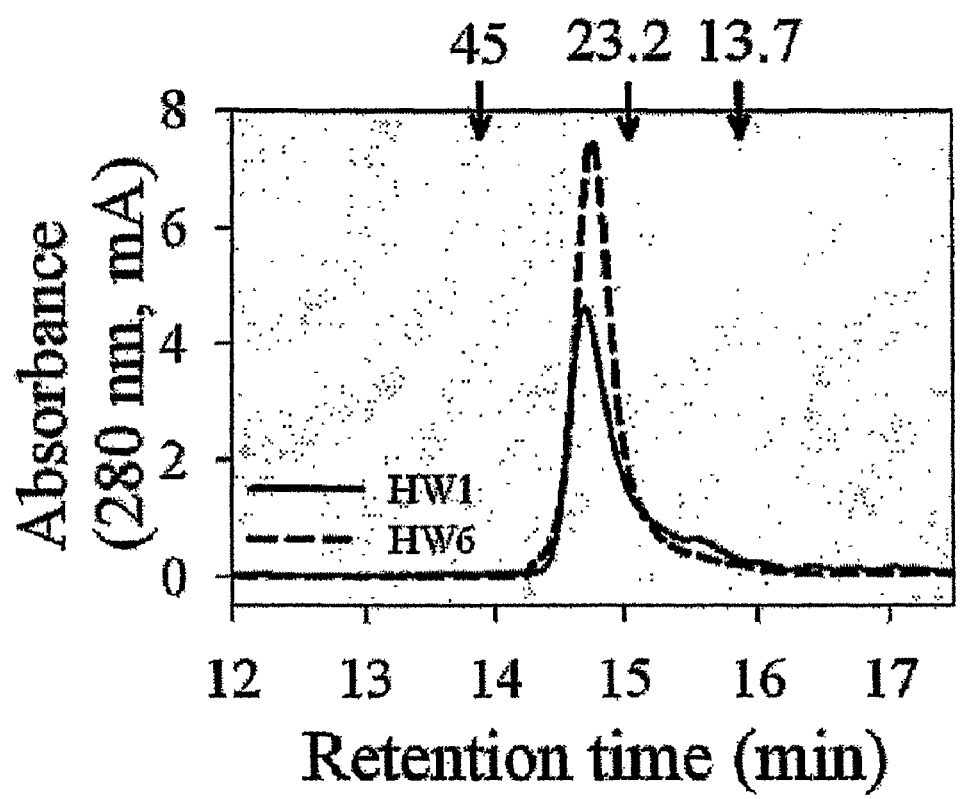
FIG. 6: the result of size-exclusion chromatography of purified HW1 and HW6.
Figure 7B:
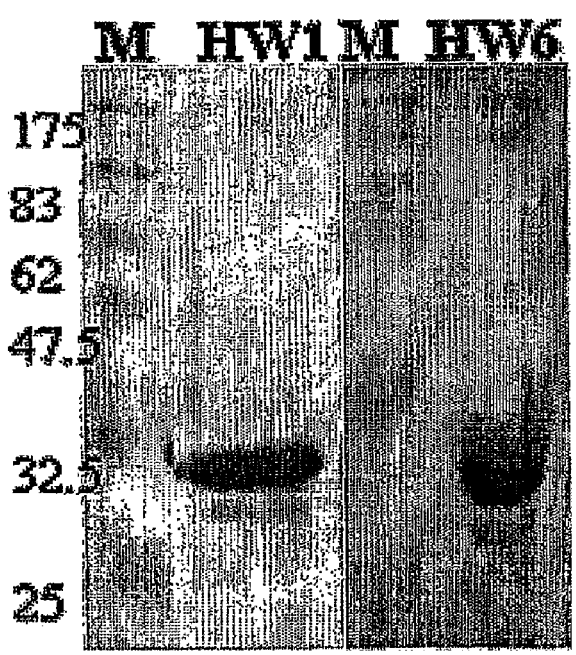

As shown in FIG. 6, HW1 and HW6 were each eluted as a monomeric form in solution at concentrations of 10 mg/ml as determined by size-exclusion chromatography. Further, there were no antibodies of the oligomeric form, which have non-native disulfide bonds, as determined by reducing SDS-PAGE (FIG. 7A) and non-reducing SDS-PAGE (FIG. 7B).

Accordingly, it was confirmed that the inventive antibody exists in the monomeric form even at a very high concentration.

TEST EXAMPLE 2

Analysis of the Binding Affinity and Cross Reactivity of Anti-DR5 scFv Antibody

The binding affinity of the anti-DR5 scFv antibody to DR5, and the cross-reactivities of the antibody with other antigens, DcR1, DcR2, DR4, TNFR1, TNFR2 and CD95 were determined by Biacore 2000 SPR (surface plasmon resonance) biosensor (Pharmacia, Sweden), respectively.

Specifically, about 0.5-1.0 mg/ml of each antigen (DR5, DcR1, DcR2, DR4, TNFR1, TNFR2 and CD95 (R&D Systems) was immobilized on a CM5 chip (carboxymethylated dextran surface chip; Pharmacia) at a level of about 2,000 to 4,000 response units in accordance with the manufacturer's instruction. Then, HW1 (200-3,200 nM) and HW6 (25-1,000 nM) each diluted with PBS (pH 7.4) was injected on the chip at 25° C. at a flow rate of 30 uQ/min to measure the degrees of interactions between the antibodies and the antigens. The surface of the chip was regenerated with 25 mM NaCl/50 mM NaOH, and the kinetic rate constants ($k_{on}$ and $k_{off}$) as well as the equilibrium dissociation constant ($K_D$) were determined by using BIA evaluation software ver. 3.2. The results are shown in Table 1, and the results of cross-reactivity are shown in FIGS. 8A to 8D.

TABLE 1

| Antibody | $k_{on}(M^{-1}S^{-1})$ | $k_{off}(S^{-1})$ | $K_D(M)$ |
|---|---|---|---|
| HW1 | $2.33 \pm 0.02 \times 10^4$ | $4.71 \pm 0.05 \times 10^{-3}$ | $2.02 \pm 0.07 \times 10^{-7}$ |
| HW6 | $1.26 \pm 0.02 \times 10^5$ | $6.88 \pm 0.17 \times 10^{-3}$ | $5.45 \pm 0.11 \times 10^{-8}$ |

Figure 8A:
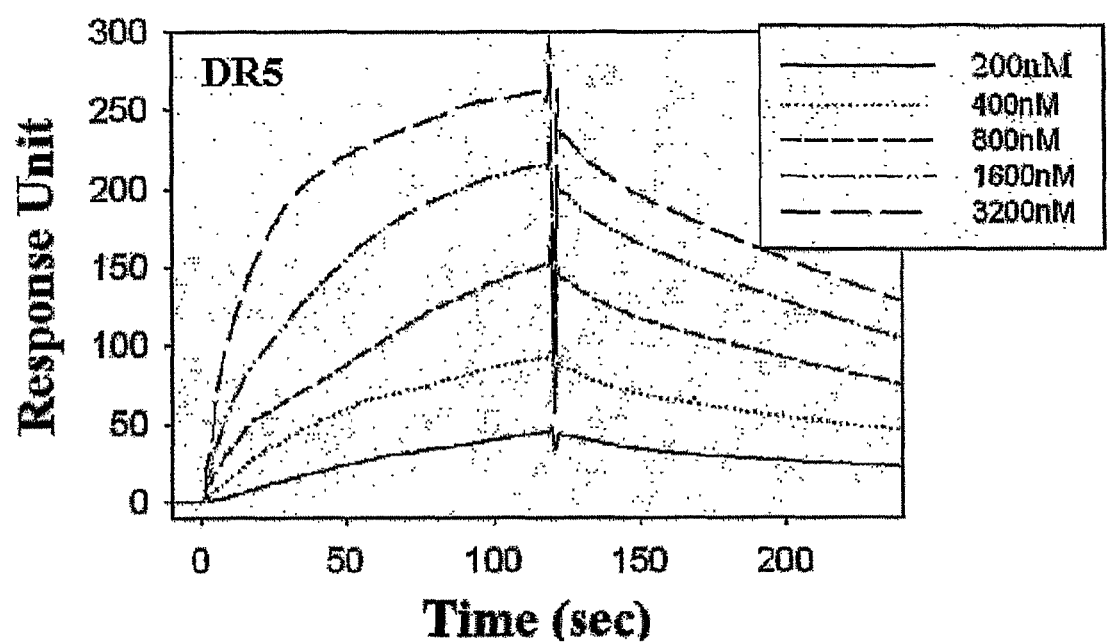
FIGS. 8A to 8D: the results of SPR (surface plasmon resonance) showing the cross reactivity of HW1 (FIGS. 8A and 8B) and HW6 (FIGS. 8C and 8D) to antigens, DR5, and DcR1, DcR2, DR4, TNFR1, TNFR2 and CD95, respectively.
Figure 8B:
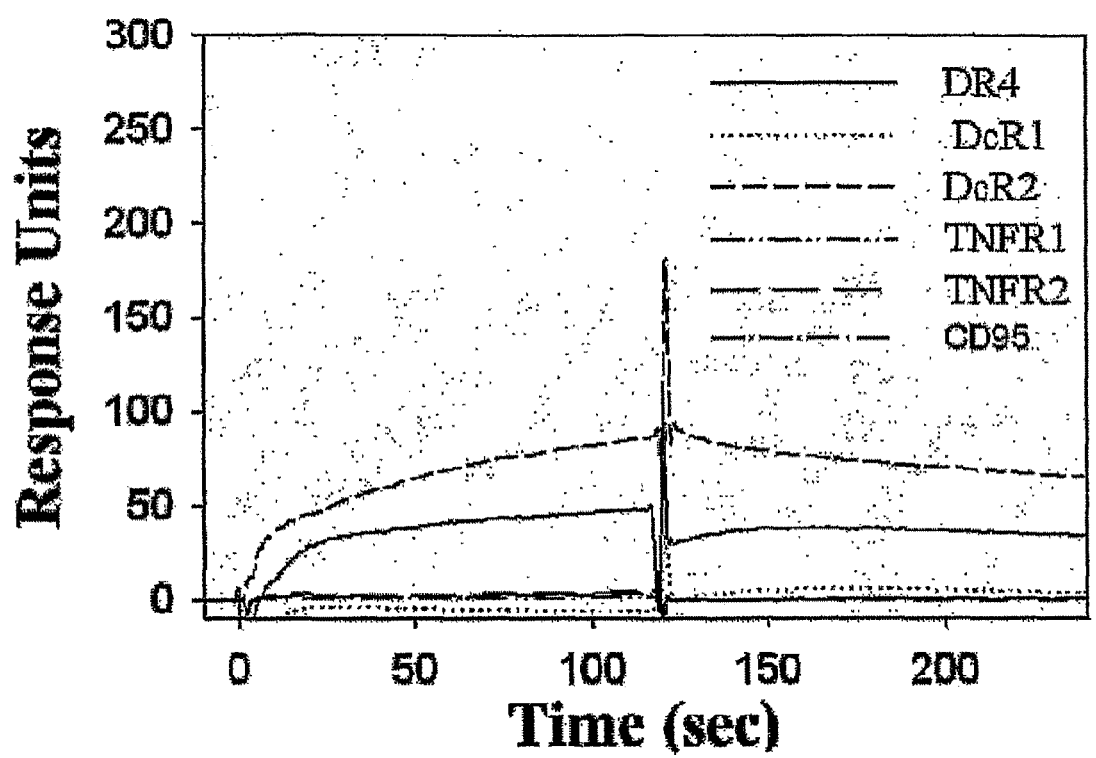
Figure 8C:
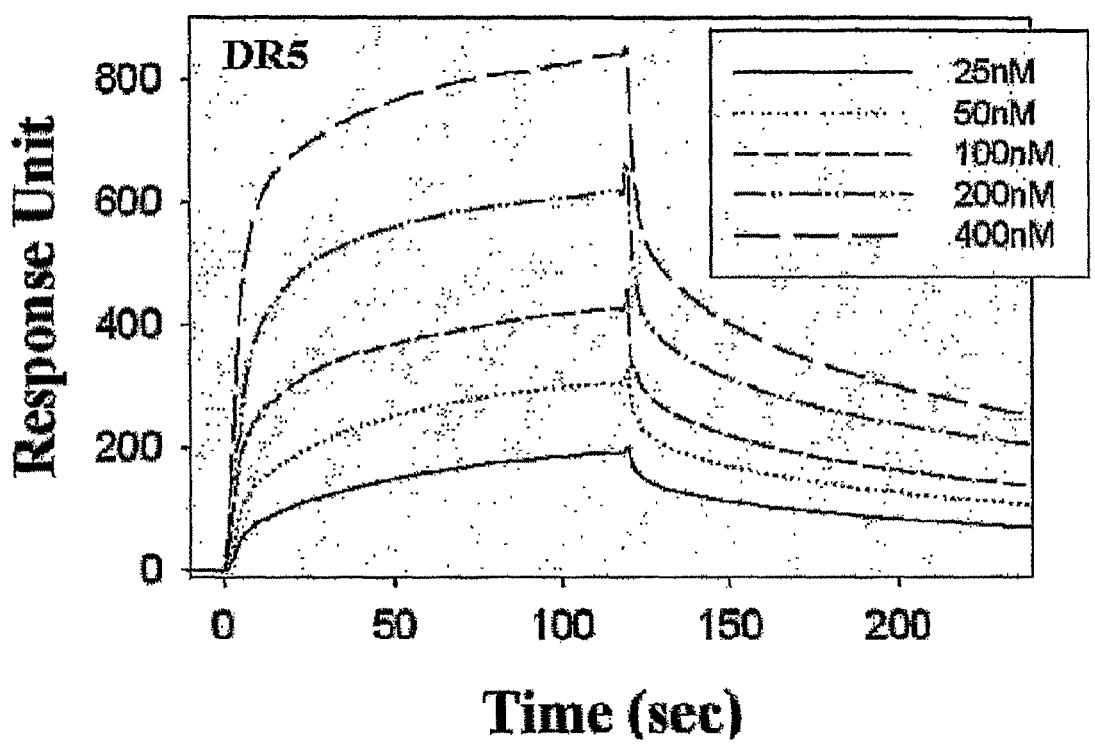
Figure 8D:
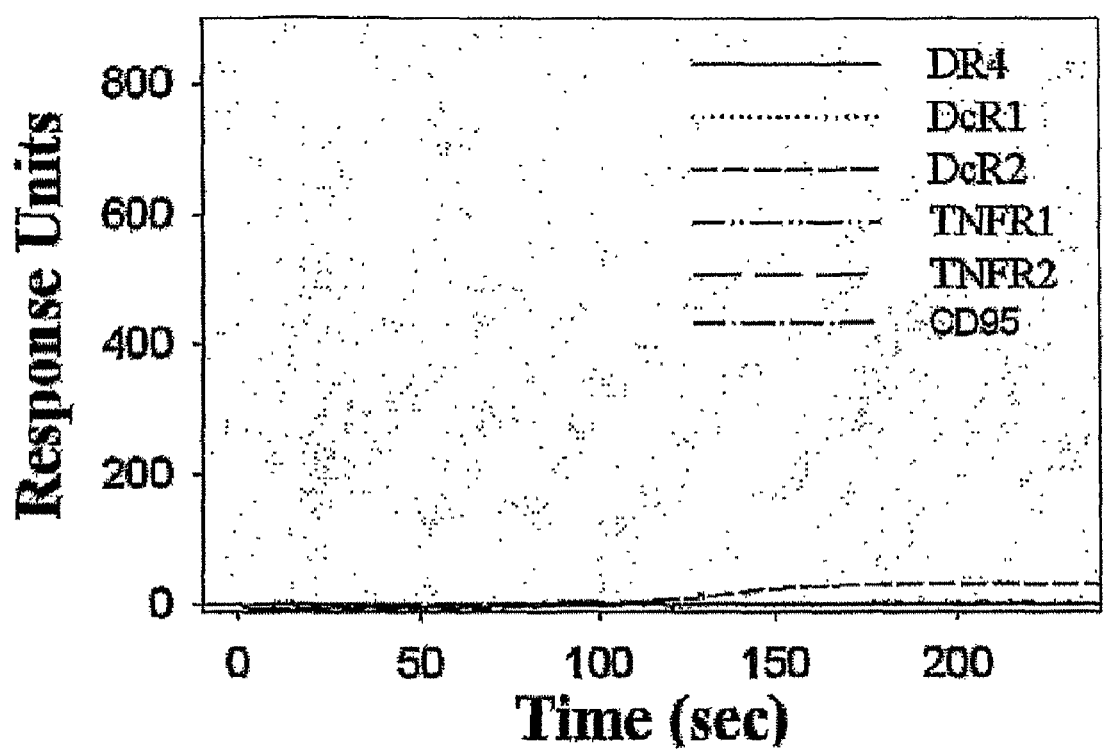

As can be seen in FIGS. 8A to 8D, HW1 and HW6 bind to DR5 with high affinities (FIGS. 8A and 8C), but they showed no affinity to DcR1, DcR2, DR4, TNFR1, TNFR2 and CD95 even at a very high concentration (up to 10 µM) (FIGS. 8B and 8D).

Accordingly, it was confirmed that the inventive HW1 and HW6 specifically bind only to DR5.

TEST EXAMPLE 3

Confirmation of the Binding of Anti-DR5 scFv Antibody to DR5 Expressed on a Cell In order to examine whether HW1 specifically binds to DR5 expressed on cell surface, plasmid T010 expressing protein DR5ΔCDYFP, which is a fusion protein of extracellular domain of DR and YFP (yellow fluorescent protein), and plasmid T30 expressing protein DcR2ΔCDYFP, which is a fusion protein of extracellular domain of DcR2 and YFP, were kindly provided by Prof. Chan (U. of Massachusetts, Mass.) (see Clancy et al., *Proc. Natl. Acad. Sci. USA*, 102:18099-18104, 2005), and transformed into HCT116 colon cancer cell (CCL-247, ATCC (American Type Culture Collection)) by electroporation to overexpress each of the proteins.

The transformed cells were seeded at a concentration of $5 \times 10^4$ cells/well to a 24-well plate, and cultured for 30 hours in an incubator under 5% $CO_2$. HW1 and TRAIL (KOMA Biotech, Korea) were stained with red fluorescence using Alexa633 labeling kit (Molecular Probes, USA), and added to the cultured transformed cells, followed by reacting the cells at 4° C. for 30 min. Each well was washed 3 times with PBS containing 2% FCS and 2% paraformaldehyde, and observed with a fluorescent microscope (LMS510 model laser scanning confocal fluorescence microscope, Carl Zeiss). The results are shown in FIGS. 9A and 9B.

Figure 9A:
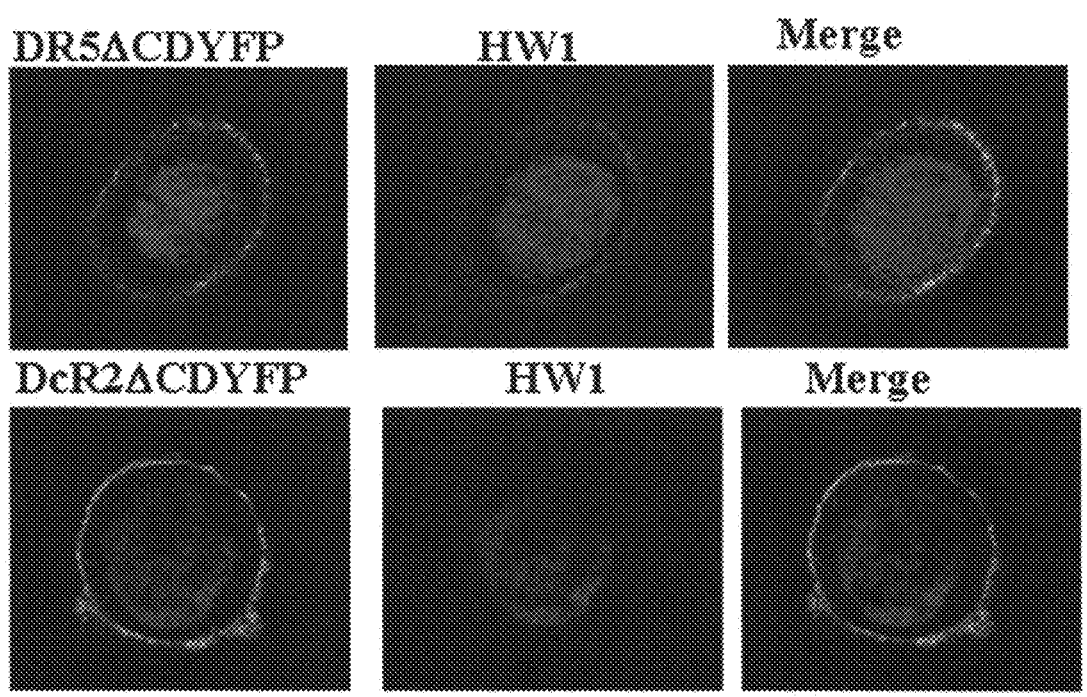
FIGS. 9A and 9B: images showing the binding of Alexa633-labeled HW1 (FIG. 9A) or TRAIL (FIG. 9B) to YFP (yellow fluorescence protein)-labeled DR5 (DR5ΔCDYFP) and DcR2 (DcR2ΔCDYFP) in HCT116 cells (human colon cancer cell)
Figure 9B:
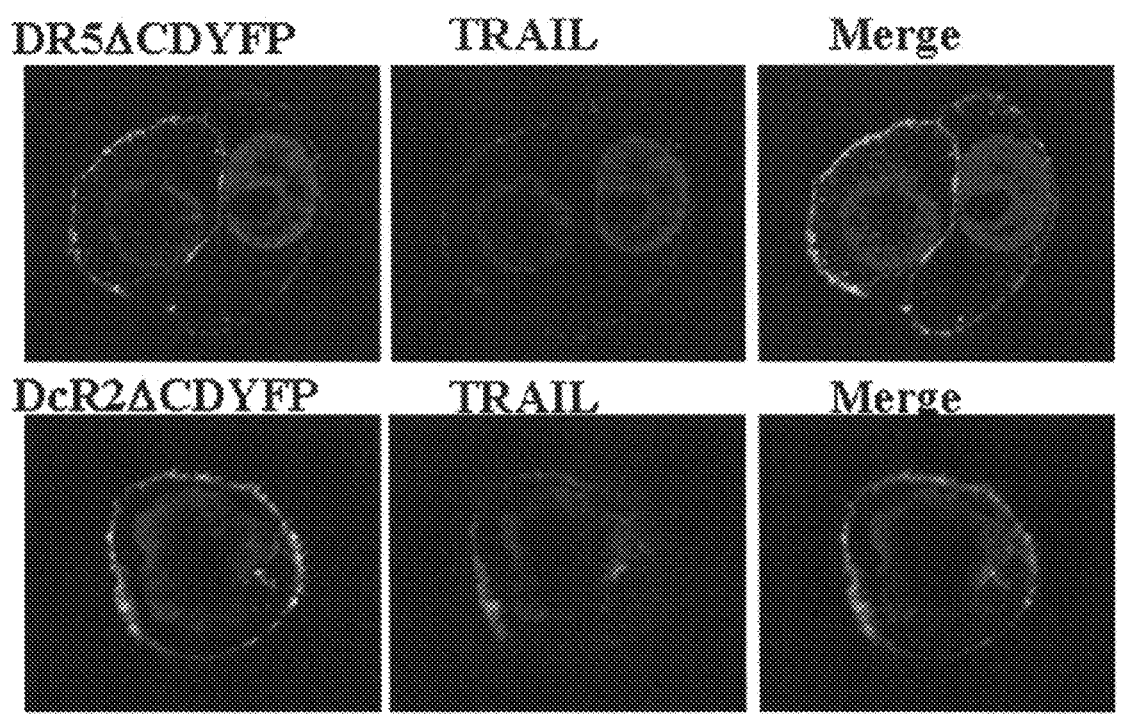

As shown in FIGS. 9A and 9B, HW1 (red) specifically binds to DR5ΔCDYFP (green) to reveal a colocalization pattern (orange), but not to DcR2ΔCDYFP (FIG. 9A). Further, TRAIL, which binds well to DR5 and DcR2, were indeed found to be bound to both DR5ΔCDYFP and DcR2ΔCDYFP (FIG. 9B).

Accordingly, it was demonstrated that HW1 antibody specifically binds to DR5 expressed on the cell membrane as well as to DR5 in solution, without any cross-reactivity.

TEST EXAMPLE 4

Identification of an Epitope of DR5 for Anti-DR5 scFv Antibody

In order to identify the binding sites (epitopes) of HW1 and HW6 to DR5, competitive ELISA with TRAIL was performed.

Specifically, each well of a 96-well plate for ELISA was coated with 50 μl of DR5 (5-20 μg/ml), followed by incubating the plate at 37° C. for 1 hour. Each well was washed 3 times with PBS, PBS containing 1% BSA was added thereto, and the plate was incubated at 37° C. for 1 hour. Then, HW1, HW1+TRAIL, HW6 and HW6+TRAIL having varying concentrations of the HW1 or HW6 in the range of $1 \times 10^{-4}$ to $1 \times 10^3$ μg/ml and 20 μg/ml of TRAIL were added to each well, and the plate was incubated at 37° C. for 1 hour and washed. Anti-Flag M2 (Sigma) or anti E-tag (Amersham), a primary antibody, was added to each well and the plate was incubated at 37° C. for 1 hour, followed by washing the plate 3 times. Then, alkaline phosphatase-conjugated anti-mouse IgG Fc specific antibody (Sigma), a secondary antibody, was added to each well and the plate was incubated at 37° C. for 1 hour, followed by washing the plate 3 times. 50 μl of p-NPP substrate was added to each well and the plate was incubated for 100 min, and the absorbance at 405 nm was measured.

Figure 10A:
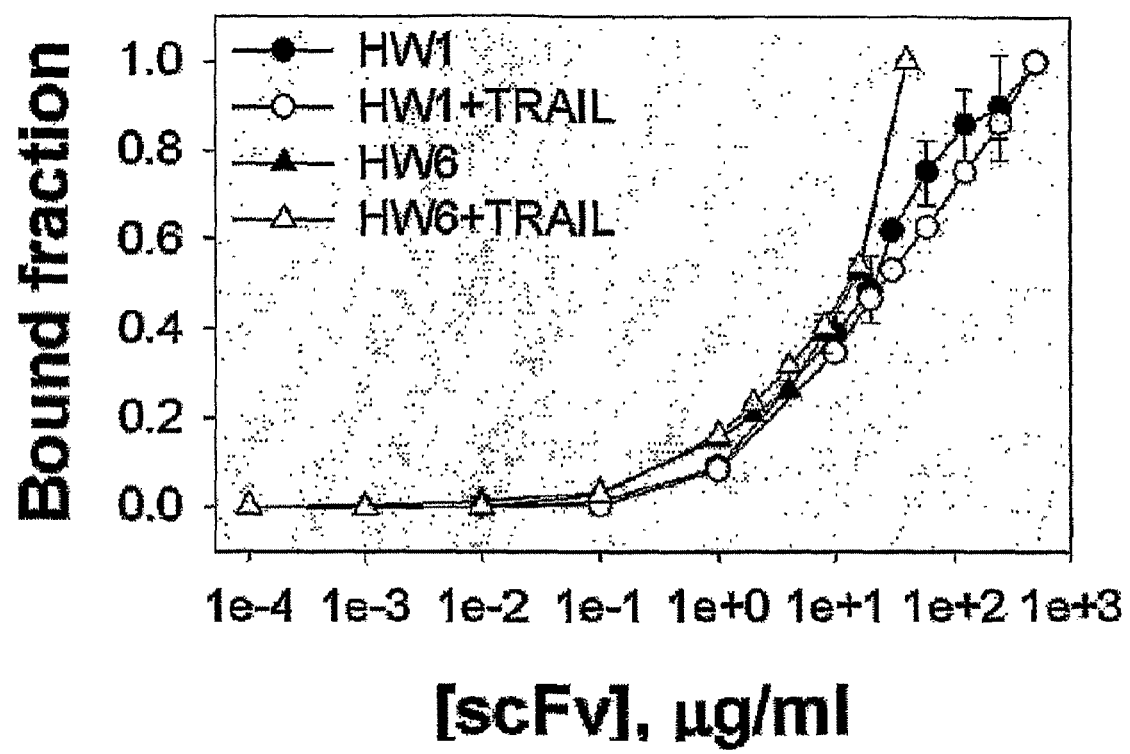
FIGS. 10A and 10B: the results of competitive ELISA examining whether or not the binding sites of HW1 and HW6 to DR5 are identical to those of TRAIL.

As shown in FIG. 10A, the binding of both HW1 and HW6 to DR5 was enhanced with the concentration of either of the antibodies regardless of the presence of TRAIL.

Further, preincubated HW1 (5 μg/μl) and HW6 (16 μg/μl) were each bound to a DR5-fixed plate, and TRAIL (0.01 μg/ml to 1,000 μg/ml) was added thereto to examine whether or not the binding of HW1 and HW6 to DR5 was changed. The result is shown in FIG. 10B.

Figure 10B:
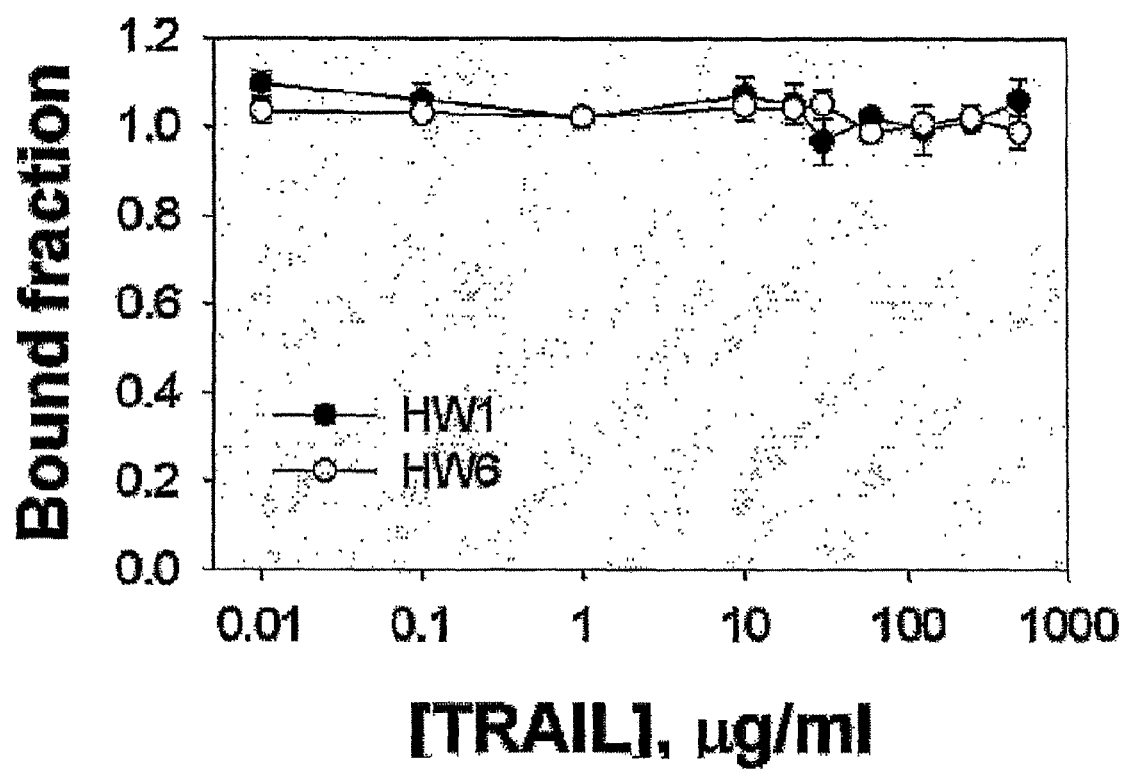

As shown in FIG. 10B, the binding of HW1 and HW6 to DR5 was not influenced by the treatment with a high concentration up to 500 ng/in of TRAIL.

Accordingly, it was confirmed that HW1 and HW6 bind to epitopes of DR5 that does not overlap with the TRAIL binding sites.

TEST EXAMPLE 5

Test of Cancer Cell Death Induced by Anti-DR5 scFv Antibody

The possibility of inducing cell death of anti-DR5 human scFv antibody, HW1 and HW6 were each evaluated using various cancer cells (ATCC), i.e., HL60 (human acute myeloid leukemia cell), HCT116 (human colon cancer cell line) and Du145 (human prostate cancer cell) for TRAIL-sensitive cells; and HepG2 and Huh7 (human hepatocellular carcinoma cancer cell), U87MG (human astrocyte cancer cell) as well as Molt-4 (Human T-lymphoblastoid leukemia) for TRAIL-resistant cells. The adherent cells such as HCT116, Du145, HepG2, Huh7 and U87MG were each incubated in DMEM medium supplemented with 10% (v/v) fetal calf serum (FCS) (Gibco Invitrogen), and the non-adherent cells such as HL60 and Molt-4 were incubated in RPMI 1640 medium supplemented with 10% FCS, 100 units/ml penicillin, and 100 μg/ml of streptomycin. The incubation was conducted at 37° C. under 5% $CO_2$.

(5-1) Cell Preparation

The cells stored in a liquid nitrogen tank was quickly thawed at 37° C., and centrifuged to remove the medium. The pellets thus obtained were mixed with the culture medium, poured in a culture flask, and cultured for 2 to 3 days. When the cell culture proceeded normally, HCT116, HepG2, Du145 and U87MG cells were each treated with 1 ml of TE buffer (Trypsin-EDTA), followed by adding 5 ml of DMEM medium containing 10% FBS to stop the reaction of TE buffer. The resulting cells were isolated by centrifugation at 1,000 rpm for 5 min. Further, HL60 and Molt-4 cells were directly recovered from the culture flask, and isolated by centrifugation at 1,000 rpm for 5 min.

Then, the cells obtained above were resuspended in the above culture medium, seeded at a density of $1 \times 10^4$ (100 μl) cells/well in a 96-well plate, and cultured for 24 hour for use in an MTT assay.

(5-2) Assay for Cell Death Induction in Trail-sensitive Cancer Cell

Purified TRAIL (0.001 to 1.0 μg/ml), HW1 and HW6 antibodies (0.05 to 50 μg/ml) were each added to a predetermined well of a 96-well plate, and MTT assay (see Muhlenbeck et al., *J Biol. Chem.*, 275:32208-32213, 2000) was conducted to measure the degree of cell death induced by the inventive antibodies of TRAIL-sensitive HL60, HCT116 and Du145 cells (FIGS. 11A and 11B).

Specifically, a MTT solution (5 mg/ml, Sigma) dissolved in 100 ml of PBS was added to each well of the plate, and the plate was incubated for 4 to 5 hours, followed by removing the culture medium and MTT solution. 200 ml of DMSO was added thereto to dissolve MTT-formazan crystals, and the absorbance thereof was read at 570 nm. In case of dealing with an anchorage-independent cell line such as HL-60, the plate was centrifuged to precipitate the cells before removing the culture medium and MTT solution, and then the supernatant was removed before measuring said absorbance.

Figure 11A:
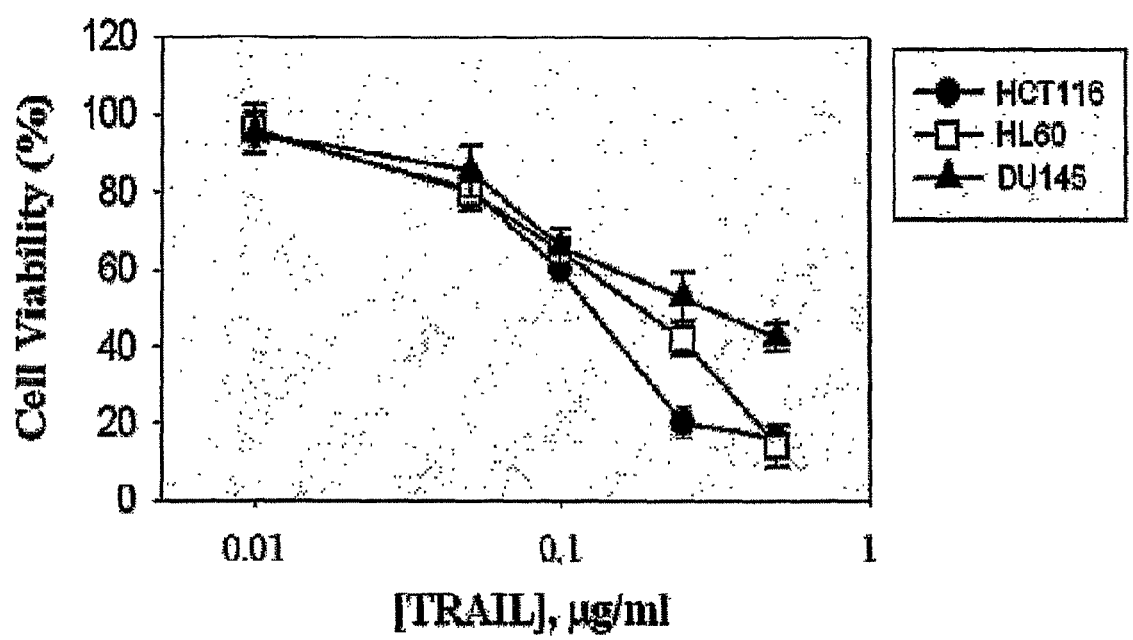
FIGS. 11A and 11B: the results of MTT assay showing the degree of cell death induced in TRAIL-sensitive HCT116, HL60 and DU145 cells as function of the concentration of TRAIL (FIG. 11A) and HW1 and HW6 (FIG. 11B)
Figure 11B:
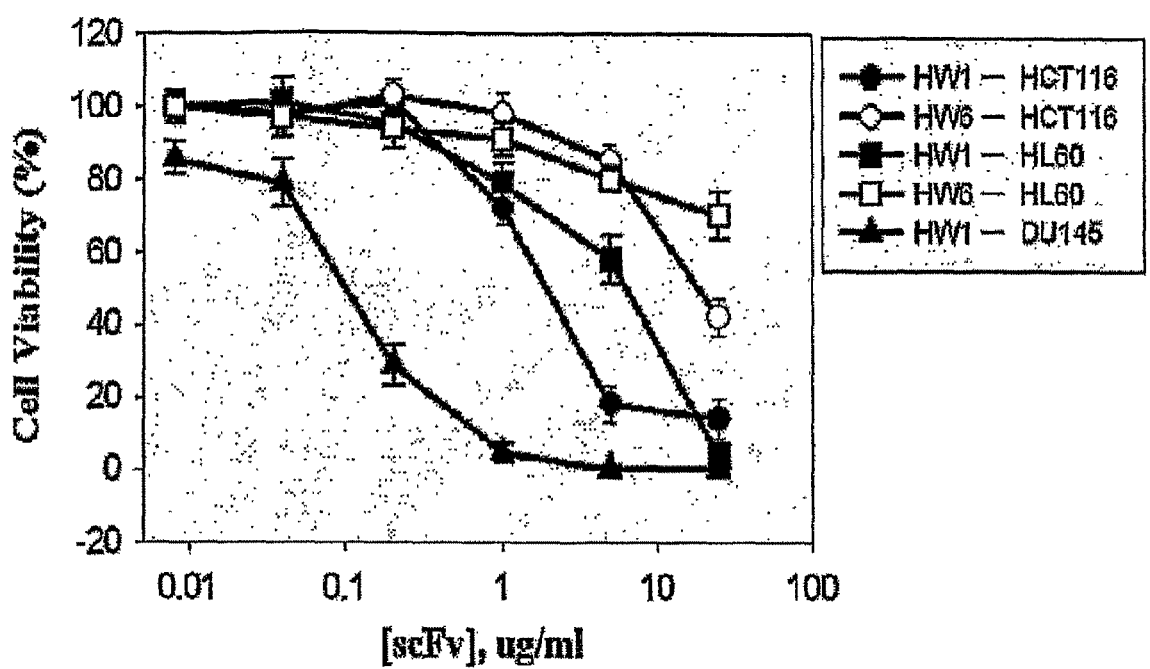

As shown in FIGS. 11A and 11B, TRAIL-sensitive cells treated with TRAIL such as HCT116, HL60 and Du145 showed effective cell death with the concentration of TRAIL (FIG. 11A), in contrast to the untreated control cells. Further, HW1 and HW6 as well as TRAIL induced cell death with the concentration of the antibodies (FIG. 11B).

Accordingly, it was confirmed that the inventive antibody in the form of a monomer alone is particularly effective in inducing cell death, which is consistent with the results of Test Example 1.

(5-3) Assay for Cell Death Induction in TRAIL-resistant Cancer Cell

MTT assay was repeated as described in (5-2) except for using TRAIL-resistant cells, HepG2, U87MG, Molt-4 and Huh7 cells. The results are shown in FIGS. 12A to 12D, and 13A and 13B.

Figure 12A:
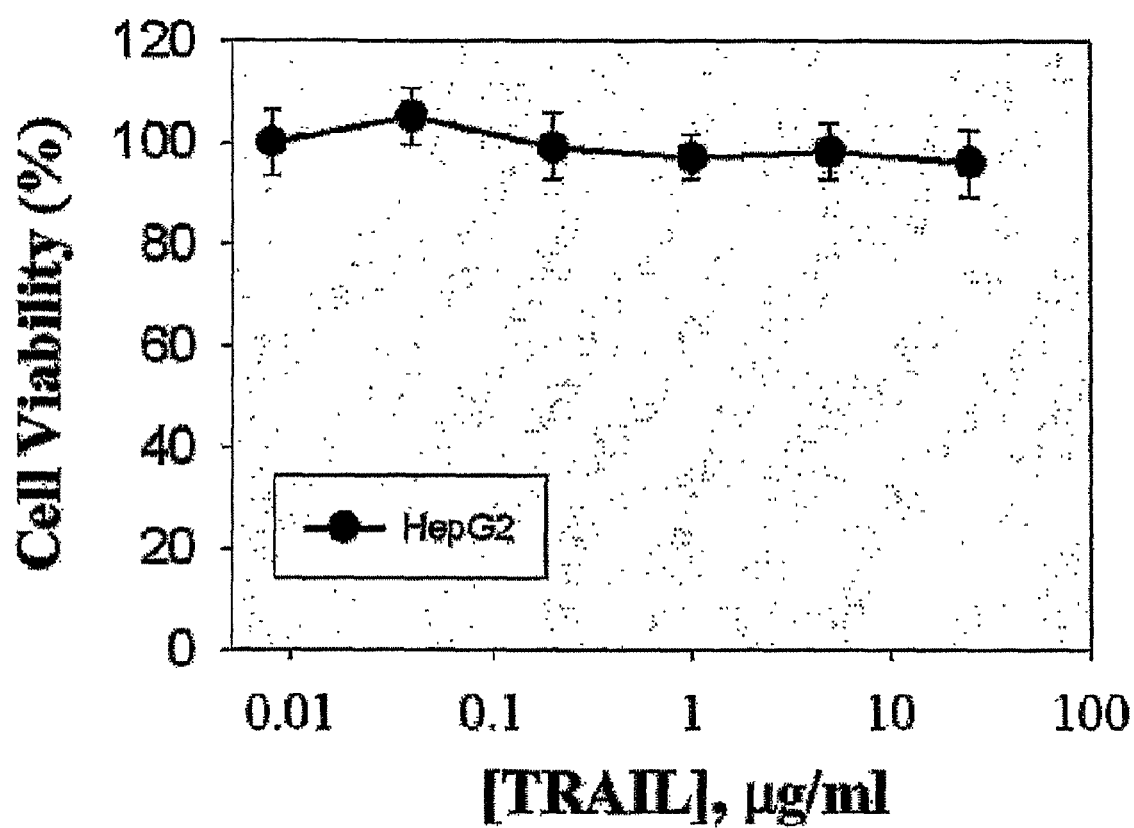
FIGS. 12A to 12D: the results of MTT assay showing the degree of cell death induced in TRAIL-resistant HepG2, U87MG and Molt-4 cells as function of the concentration of TRAIL (FIGS. 12A and 12C) and HW1 and HW6 (FIGS. 12B and 12D)
Figure 12B:
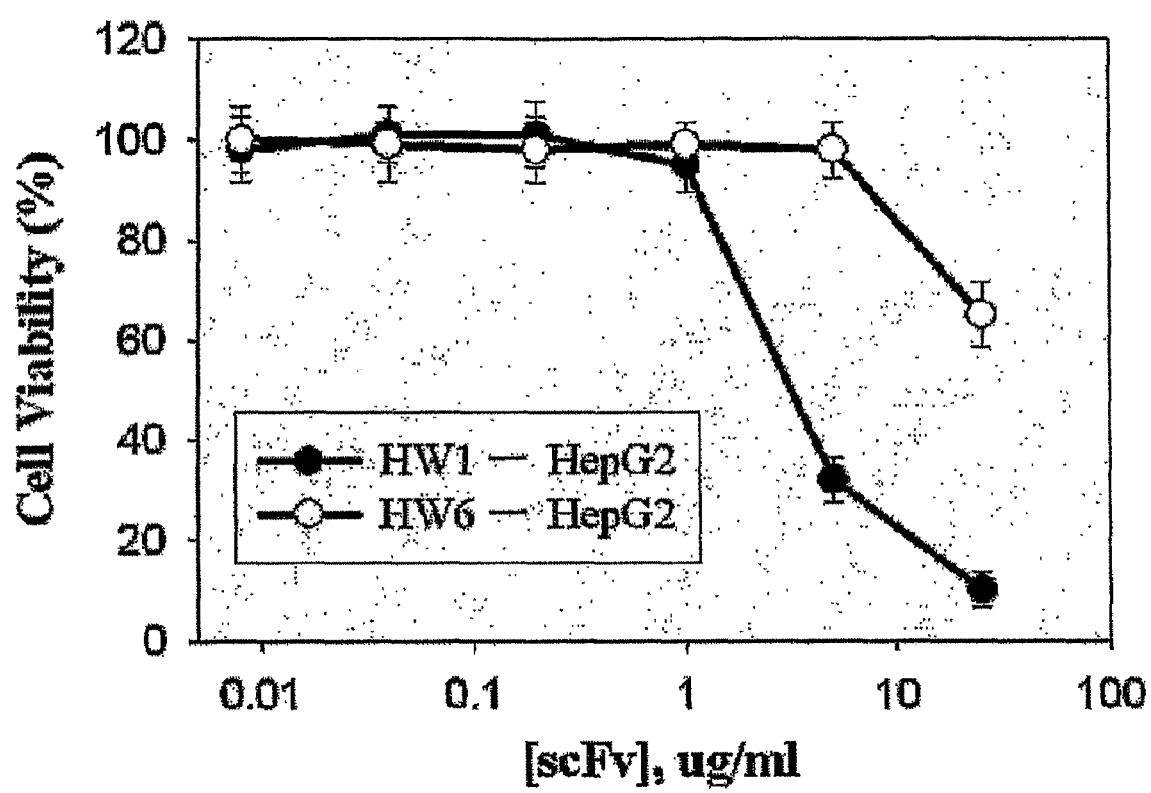
Figure 12C:
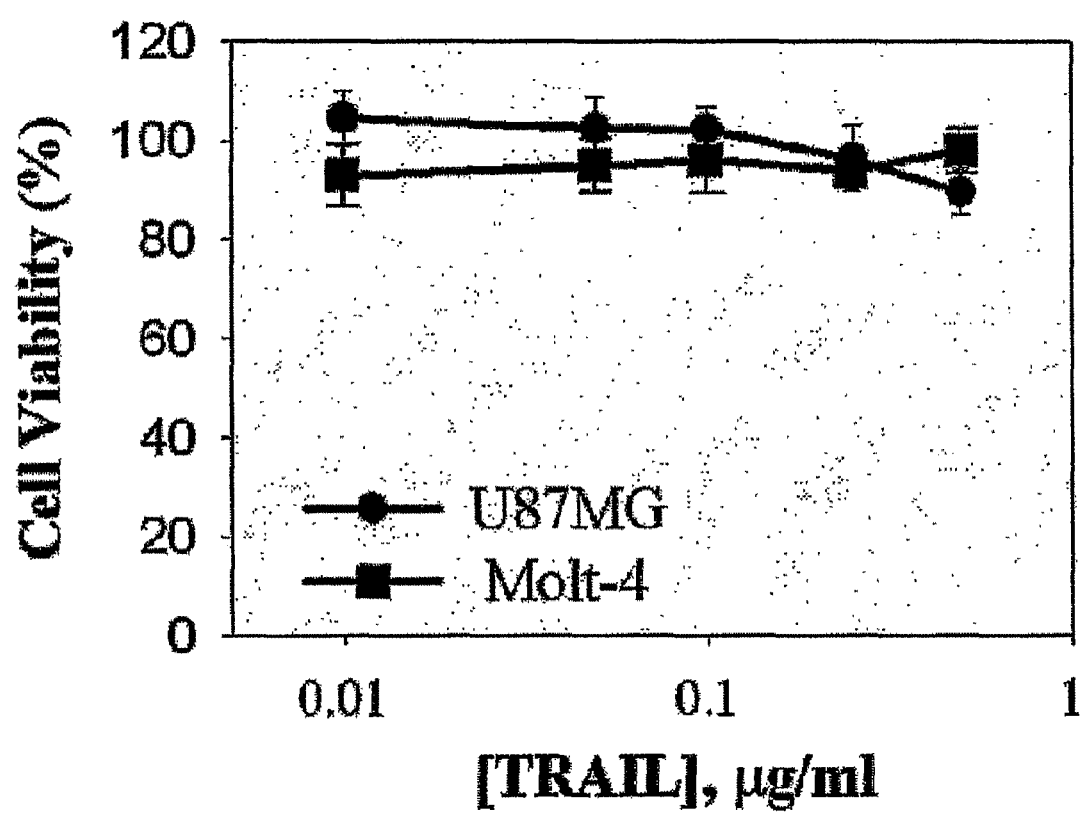
Figure 12D:
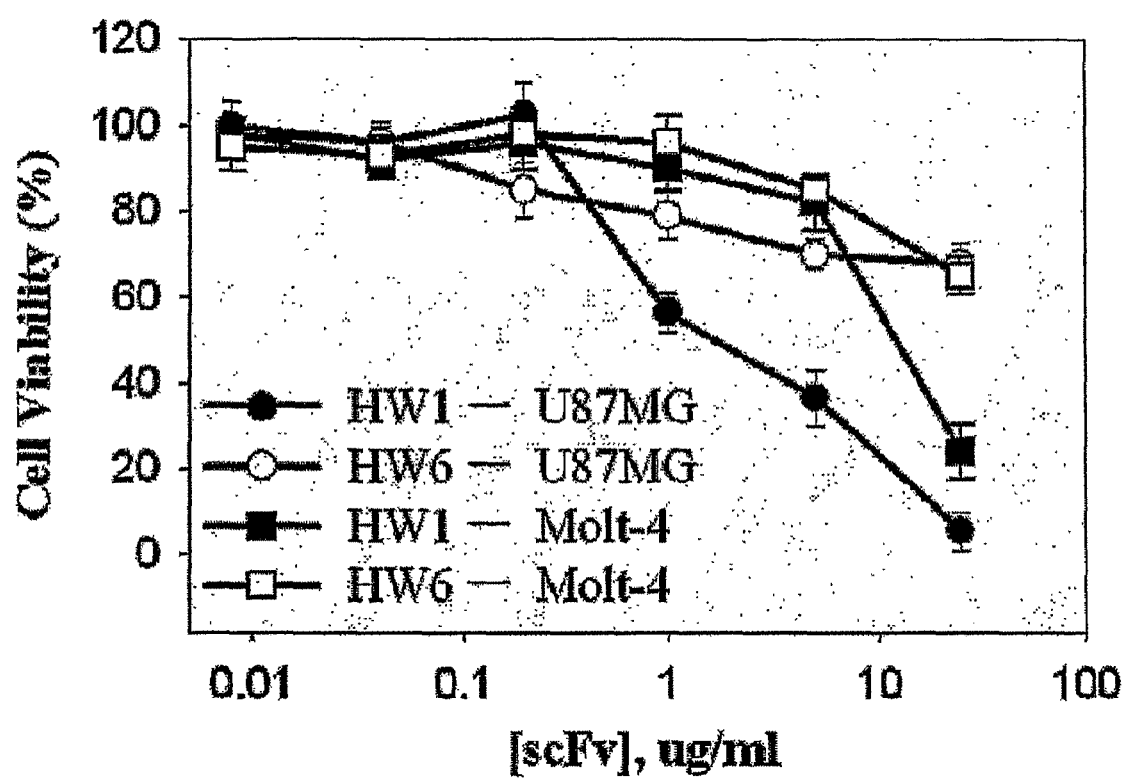

As shown in FIGS. 12A to 12D, TRAIL treated TRAIL-resistant cells such as HepG2, U87MG and Molt-4 did not show any cell death (FIGS. 12A and 12C), while HW1 or HW6-treated cells showed significant cell death (FIGS. 12B and 12D).

Anti-DR5 IgG mAb showing cytotoxicity in TRAIL-sensitive cancer cells has recently been reported, but an antibody showing cytotoxicity toward TRAIL-resistant cancer cells has not yet been reported.

Figure 13A:
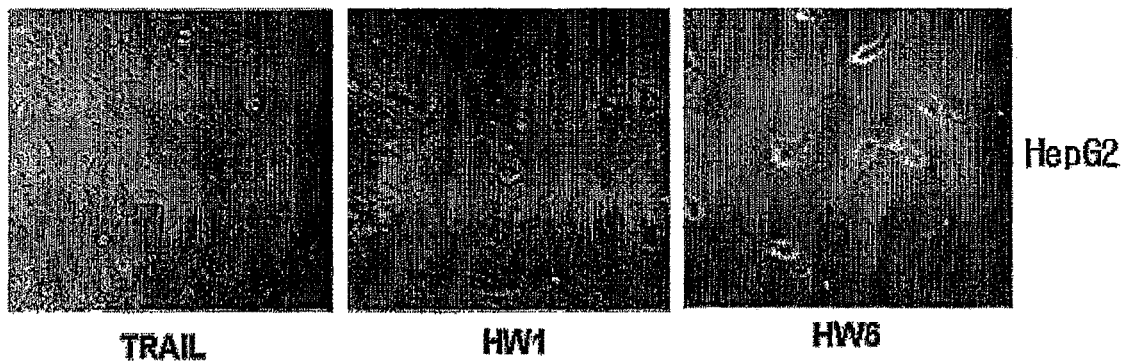
FIGS. 13A and 13B: microscopic images showing the cell death induced in TRAIL-resistant HepG2 cells (FIG. 13A) and Huh7 cell (FIG. 13B) by TRAIL, HW1 and HW6.
Figure 13B:
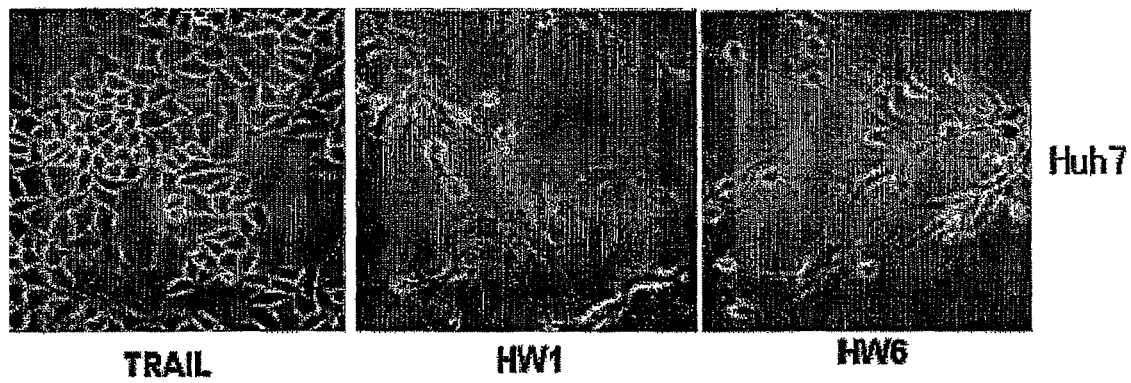

Further, as shown in FIGS. 13A and 13B, when HW1 (25 μg/lni) or HW6 (25 μg/ml) was used to treat TRAIL-resistant HepG2 cells (FIG. 13A) and Huh7 cells (FIG. 13B) for 20 hours, cell death was observed, the dead cells being detached from culture plates, but TRAIL (500 ng/ml)-treated cells remained unharmed.

Accordingly, it was confirmed that the inventive antibody of the monomeric form induces death of cancer cells, especially TRAIL-resistant cells.

(5-4) Assay for Cell Death Induction in Normal Cell

In order to evaluate the cytotoxicities of HW1 and HW6 for normal cells, cell culture, MTT assay and cell observation were conducted as described in (5-1) and (5-2) except for using normal human hepatocytes and mammary epithelial cells (Cambrex BioScience) as well as brain astrocyte (see Kim et al., *Oncogene*, 24:838-849, 2005). The results are shown in FIGS. 14A and 14B, and 15.

Figure 14A:
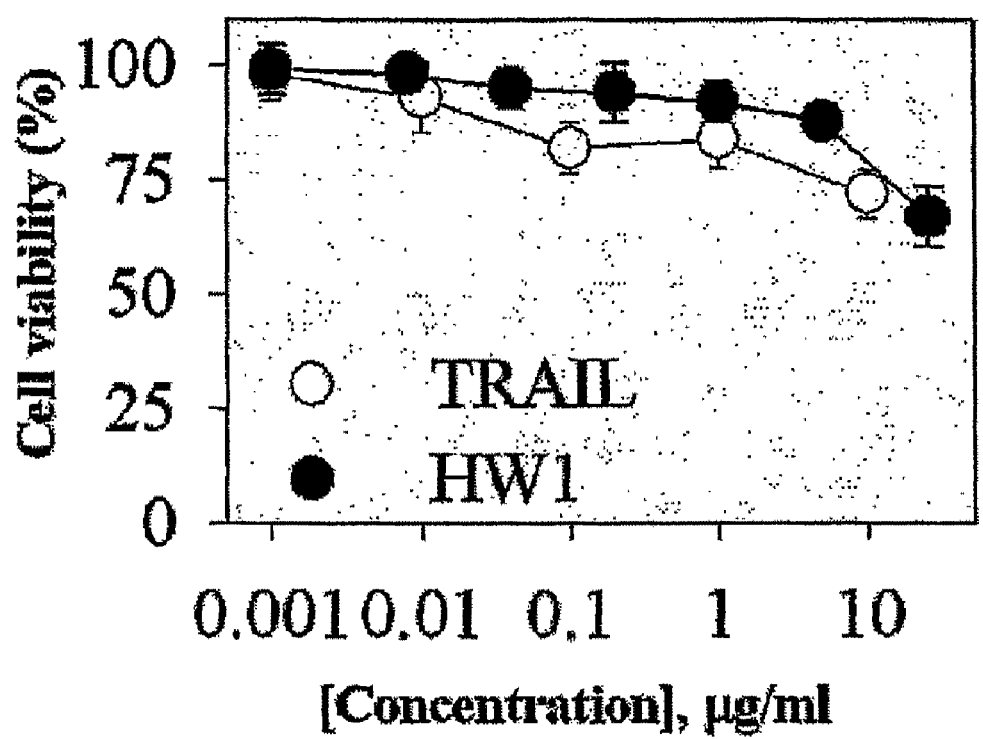
FIGS. 14A and 14B: the results of cytotoxicity test showing that no cytotoxicity to normal human cells, hepatocytes (FIG. 14A) and mammary epithelial cells (FIG. 14B) was caused by increased concentration of TRAIL and HW1.
Figure 14B:
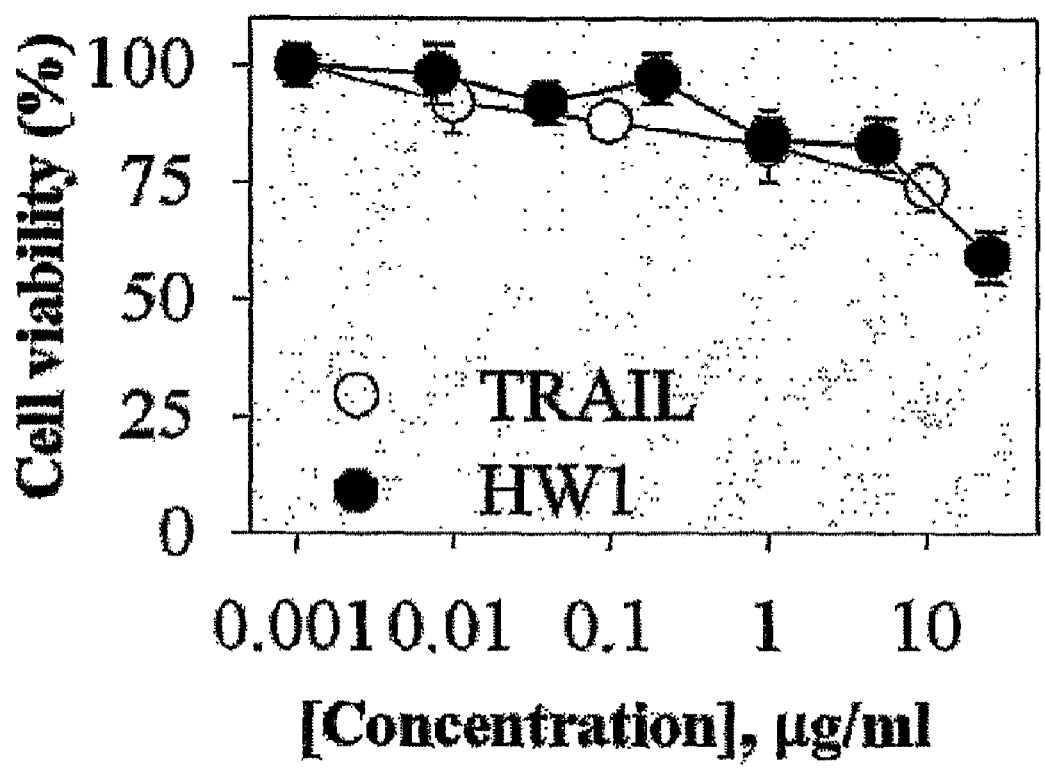

As shown in FIGS. 14A and 14B, when human hepatocytes (FIG. 14A) and mammary epithelial cells (FIG. 14B) were treated with HW1 or TRAIL at varying concentration for 30 hours, HW1 as well as TRAIL induced about 30% cell death at a high concentration, but did not induce cell death at a lower concentration. Accordingly, it was confirmed that HW1 exerted lesser cytotoxicity in normal cells.

Further, as shown in FIG. 15, the treatment with HW1 (40 μg/mg) or HW6 (40 μg/ml) of normal brain astrocytes at a high concentration for up to 48 hours did not induce any cell death.

Accordingly, it was demonstrated that the inventive antibodies induce cell death only in cancer cells, but exhibit no cytotoxicity in normal cells.

TEST EXAMPLE 6

Test of Cancer Cell Death Through DR5 Induced by Anti-DR5 scFv Antibody (6-1) Test of Cell Death in HCT116 Cell Expressing DR5

In order to check whether or not HW1 induces cell death through DR5 expressed on cell surface, various concentration of a soluble competitor of DR5—Fc conjugated protein (DR5 fused to antibody constant region Fc) was added to TRAIL (100 ng/ml) or HW1 (5 μg/ml), and cell death inhibition was assessed while incubating the mixture for 30 hours. The result is shown in FIG. 16.

Figure 16:
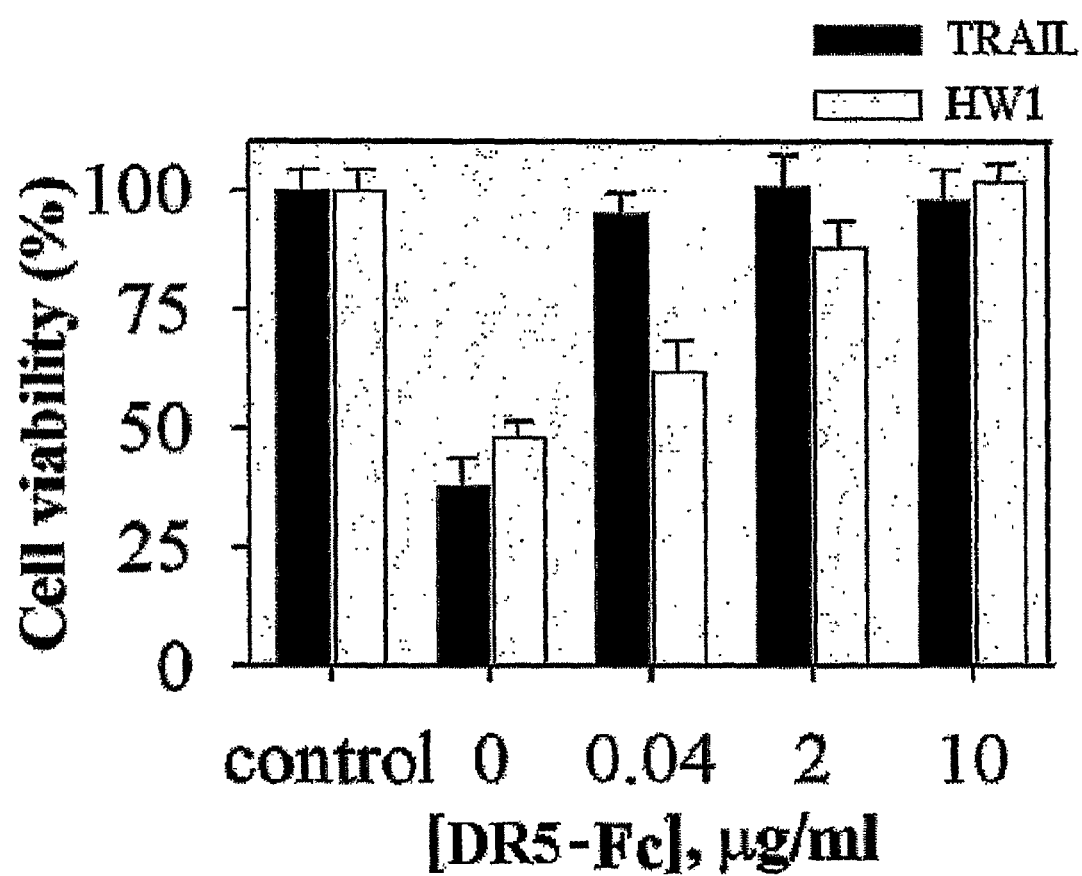
FIG. 16: the result of MTT assay to quantify the cytotoxicity of varying concentration of HW1 and TRAIL in HCT116 cells, after treating cell membrane-expressed DR5 and soluble competitor DR5—Fc.

As shown in FIG. 16, cell death mediated by either TRAIL or HW1 was gradually inhibited with concentrations of DR5—Fc, and cell death was completely inhibited with 10 μg/ml of DR5—Fc.

Accordingly, it was confirmed that HW1 as well as TRAIL induces cell death by the specific binding to DR5 expressed on cell surface.

(6-2) Test of Cell Death Induced in HCT116 Cell Overexpressing DR5

In order to check whether or not HW1 induces cell death of DR5 overexpressed cancer cell, HCT116 cancer cells were incubated, and treated with sulforaphane (10 μM) for 9 hours to overexpress DR5 (see Kim et al., *Cancer Res.*, 66:1740-1750, 2006). 0.01 to 10 μg/ml of TRAIL or HW1 was added to the cells, incubated for 30 hours, and MTT assay was performed to analyze the degree of cancer cell death. The result is shown in FIG. 17.

Figure 17:
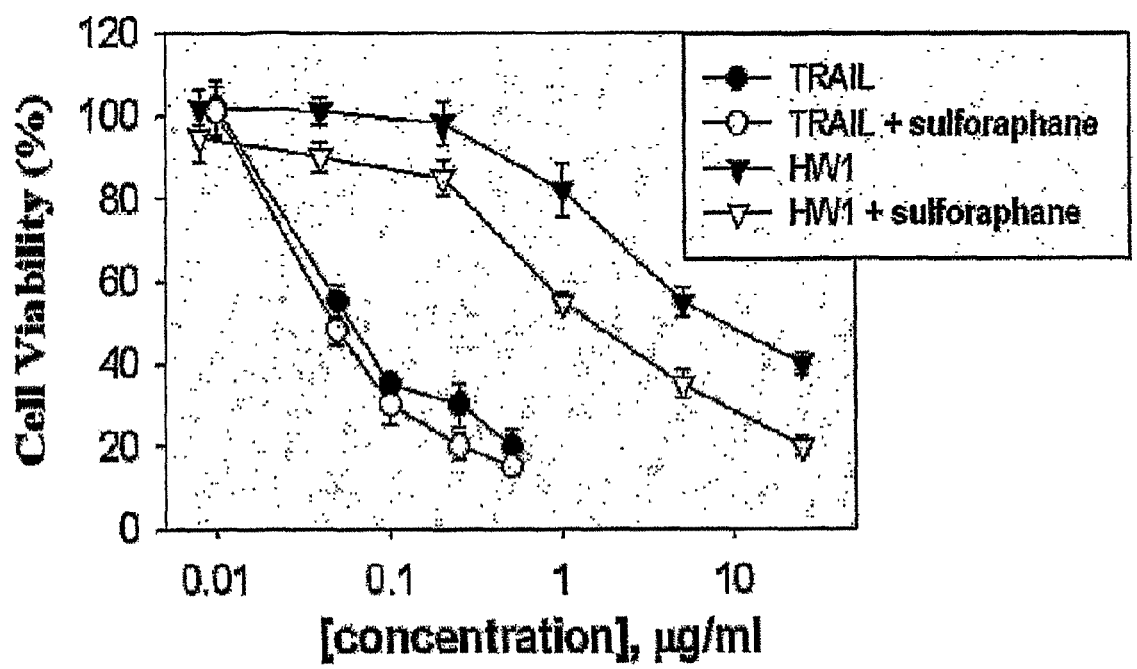
FIG. 17: the result of MTT assay to quantify cell death by TRAIL and HW1 of TRAIL-sensitive HCT116 cells in the presence or absence of sulforaphane.

As shown in FIG. 17, both TRAIL and HW1 showed enhanced cell death activity for sulforaphane-treated cells, compared with the untreated control cells.

Accordingly, it was proved that HW1 induces cancer cell death through cell death signaling transduction through the specific binding to DR5.

TEST EXAMPLE 7

Evaluation of Influence of a Cross-linker on Cancer Cell Death Induced by Anti-DR5 scFv Antibody Some anti-DR5 antibodies as IgG form having divalent binding sites have induced cell death, but their respective monovalent Fab form could not (see Motoki et al., *Clin. Cancer Res.*, 11:3126-3135, 2005; and Wajant et al., *Oncogene*, 20:4101-4106, 2001). Therefore, in order to check whether or not the inventive antibody induces cell death as a monomeric form as well as oligomeric form, 6× His tagged HW1 was mixed with mouse derived anti-His6 IgG as a cross-linker (1:1 molar concentration), and the mixture was incubated at 4° C. for 1 hour to form an oligomeric molecule. The molecule was added to TRAIL-sensitive HCT116 cells and TRAIL-resistant HepG2 cells, and the cells were incubated for 30 min. MTT assay was conducted as described in (5-2) of Test Example 5, and the result is shown in FIG. 18.

Figure 18:
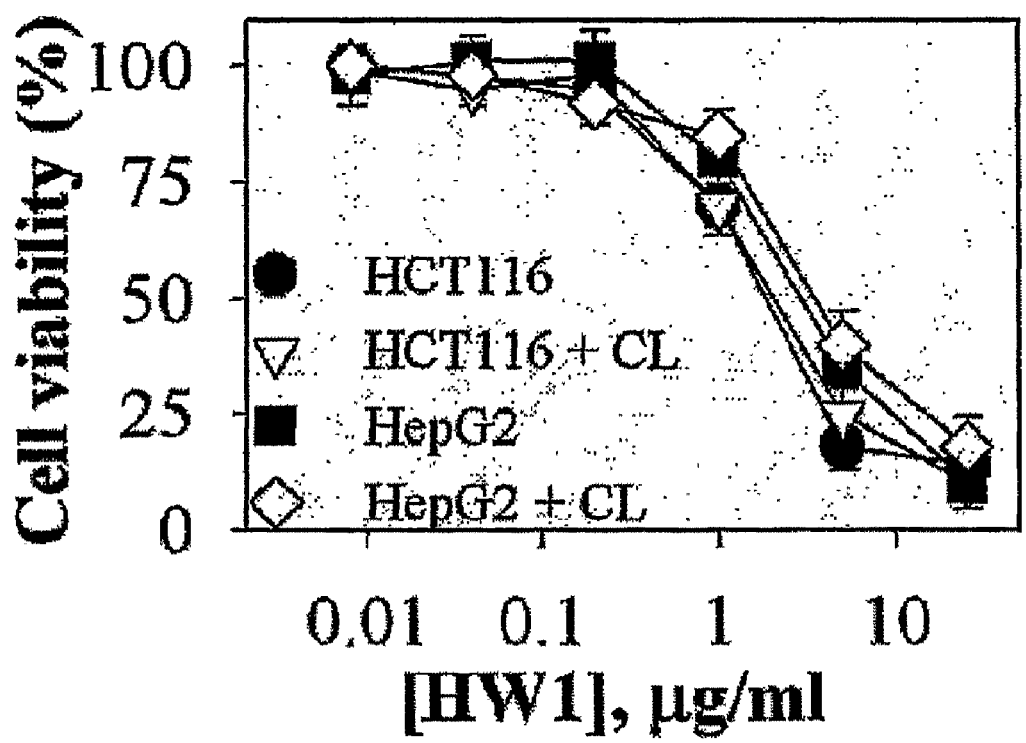
FIG. 18: the result of MTT assay to quantify the cytotoxicity of HW1 for TRAIL-sensitive HCT116 cells and TRAIL-resistant HepG2 cells in the presence or absence of a cross-linker (CL)

As shown in FIG. 18, both cells induced cell death regardless of treatment of a cross-linker.

Accordingly, it was proved that HW1 induces cell death of cancer cells as a monomeric form.

TEST EXAMPLE 8

Study of Cell Death Mechanism of Anti-DR5 scFv Antibody

In order to identify which cell death pathway is used for HW1-induced cell death of cancer cells, the following experiments were performed.

(8-1) Transmission Electron Microscopy (TEM)

TRAIL-sensitive HCT116 and Du145 cells, and TRAIL-resistant Hep2 and U87MG cells were incubated with TRAIL (0.2 μg/ml) and HW1 (25 μg/ml) for 5 hours and 30 hours, respectively, and prefixed with Karnovsky's solution (2% glutaraldehyde and 1% paraformaldehyde in 100 mmol/l sodium cacodylate buffer, pH 7.4) at 25° C. for 2 hours. The cells were washed with 100 mmol/l sodium cacodylate buffer containing 2% glutaraldehyde and 1% paraformaldehyde (pH 7.4), postfixed with 1% osmium tetroxide and 1.5% potassium ferrocyanide for 1 hour, dehydrated by a graded series of ethanol (50-100%), embedded on Poly Bed 812 resin (Pelco, Canada), cut into ultrathin slices using a ultramicrotome (Reichert Ultracut E microtome), and observed under an electron microscope (EM 902A, Carl Zeiss, Germany). The results are shown in FIGS. 19A to 19D.

Figure 19A:
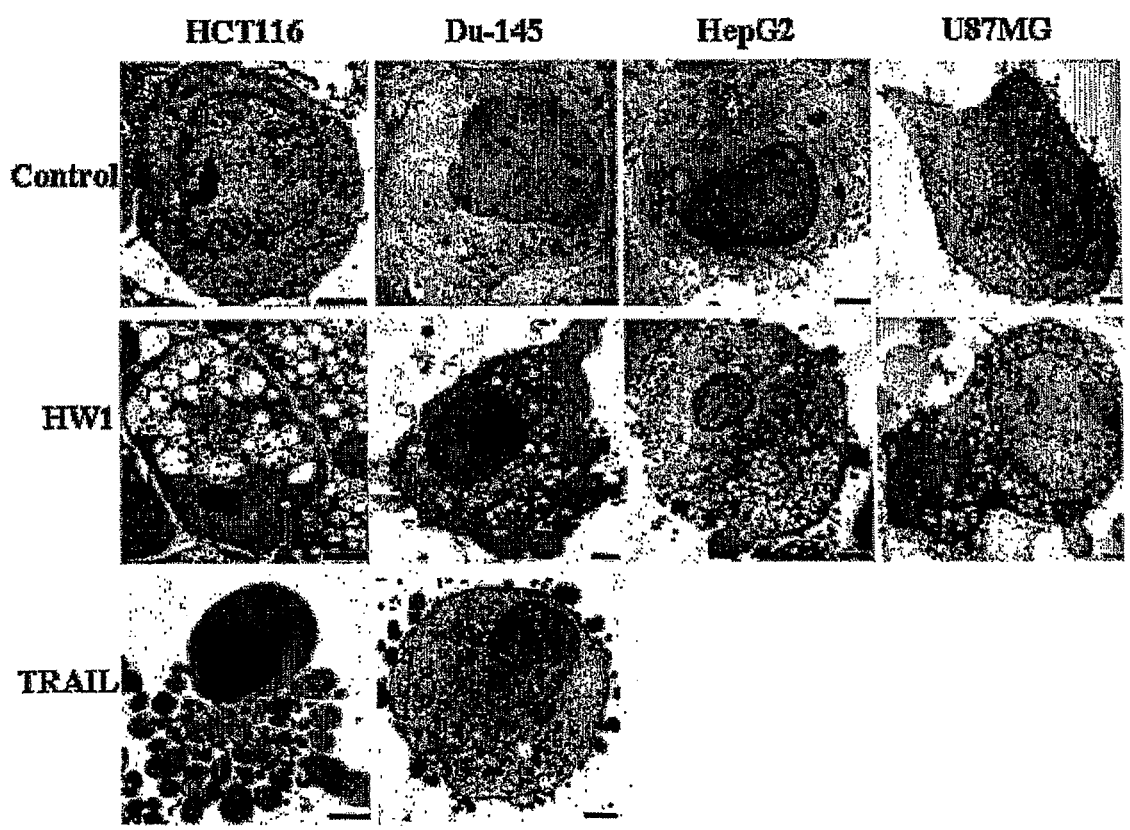
FIGS. 19A to 19D: microscopic images showing that cell death of TRAIL-sensitive cells (HCT116 and Du145) and TRAIL-resistant cells (HepG2 and U87MG) induced by HW1 is autophagic cell death (wherein, FIG. 19A is TEM images, FIGS. 19B to 19D are high-magnification images showing multiple-membrane-bound autophagic vacuoles, double-membrane-bound autophagic vacuoles, and autophagic vacuole induction step by fusing empty vacuoles with vacuoles containing cellular organelles, respectively)
Figure 19B:
Figure 19C:
Figure 19D:
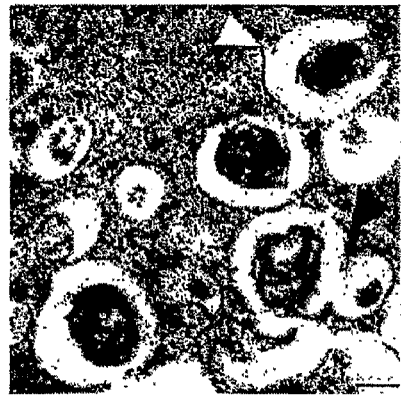

As shown in FIGS. 19A to 19D, TRAIL-sensitive cancer cells treated with TRAIL showed typical characteristics of apoptotic cell deaths such as chromatic condensation and membrane blebbing. However, both TRAIL-sensitive and -resistant cells treated with HW1 exhibited numerous autophagic vacuoles in the cells and damaged cellular organelles such as mitochondria (FIG. 19A).

Further, in higher magnificated images, multiple- and double-membrane-bound autophagic vacuoles (FIGS. 19B and 19C), and autophagic vacuole induction step by fusing empty vacuoles with vacuoles containing cellular organelles (FIG. 19D) were observed in both cells. These characteristics indicated that the cell death was caused by autophagic cell death surely distinguished from apoptosis (see Kondo et al., *Nat. Rev. Cancer*, 5:726-734, 2005; and Tsujimoto et al., *Cell Death Differ.*, 2:1528-1534, 2005).

Accordingly, it was confirmed that cell death of various cancer cells induced by the inventive antibodies is resulted from autophagy. This fact is first reported for anti-DR5 antibody, and supports that a DR5 receptor can kill TRAIL-resistant cancer cells through autophagic cell death as well as apoptosis.

(8-2) Specific Autophagic Vacuole Staining Using Lysotracker-red

Autophagic cell death can be confirmed by using lysotracker-red (DND-99, Molecular probes), which specifically stains autophagic vacuoles (see Kondo et al., *Nat. Rev. Cancer*, 5:726-734, 2005; and Tsujimoto et al., *Cell Death Differ.*, 2:1528-1534, 2005).

Therefore, TRAIL-sensitive HCT116 cells and TRAIL-resistant U87MG cells were treated with HW1 (25 μg/ml) for 20 hours, fixed, stained with lysotracker-red, and observed under a fluorescence microscope. The results are shown in FIGS. 20A and 20B.

Figure 20A:
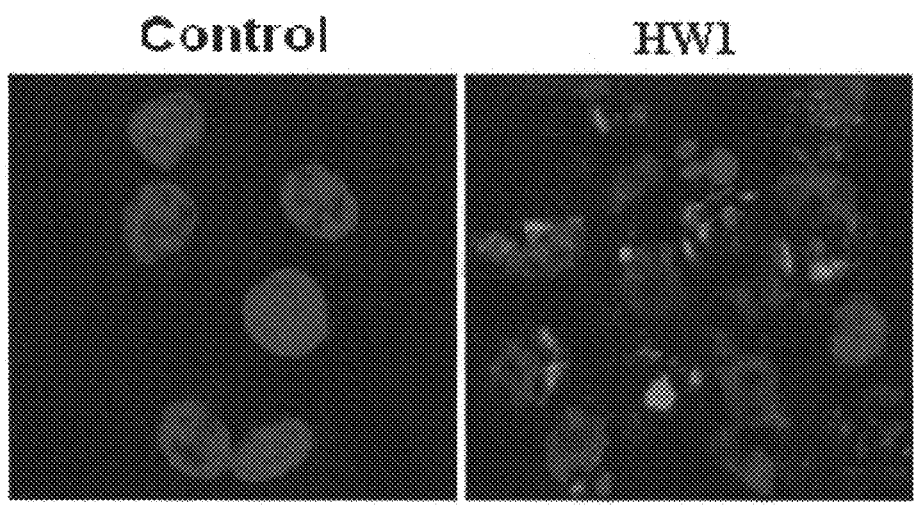
FIGS. 20A and 20B: fluorescent microscopic images obtained using lysotracker-red DND-99 which specifically stains cellular autophagic vacuoles, showing autophagic cell death induced by HW1 on TRAIL-sensitive HCT116 cells (FIG. 20A) and TRAIL-resistant U87MG cells (FIG. 20B).
Figure 20B:
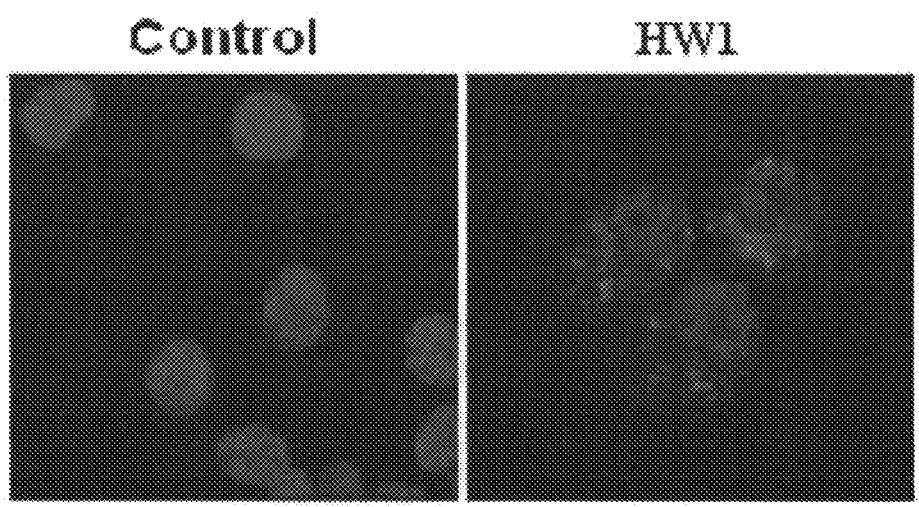

As shown in FIGS. 20A and 20B, specifically stained autophagic vacuoles were observed in both HCT116 cells (FIG. 20A) and U87MG cells (FIG. 20B) treated with HW1.

Accordingly, it was proved that HW1 induces autophagic cell death of cancer cells.

While the invention has been described with respect to the above specific embodiments, it should be recognized that various modifications and changes may be made and also fall within the scope of the invention as defined by the claims that follow.

What is claimed is:

1. An isolated antibody which specifically binds to death receptor 5 (DR5) selected from the group consisting of: an antibody comprising a heavy chain variable region ($V_H$) having the amino acid sequences of SEQ ID NOs: 1 to 3 at complementary determining regions (CDRs) and a light chain variable region ($V_L$) having the amino acid sequences of SEQ ID NOs: 4 to 6 at CDRs; and an antibody comprising a $V_H$ having the amino acid sequences of SEQ ID NOs: 7 to 9 at CDRs and a $V_L$ having the amino acid sequences of SEQ ID NOs: 10 to 12 at CDRs.

2. The isolated antibody of claim 1, which induces cell death of TRAIL-sensitive and TRAIL-resistant cancer cells expressing DR5.

3. The isolated antibody of claim 1, which is a whole antibody selected from the group consisting of IgG, IgM, IgA, IgD and IgE.

4. The isolated antibody of claim 1, which is an antibody fragment selected from the group consisting of single chain variable fragment (scFv), (scFv)$_2$, Fab, Fab', F(ab')$_2$ and scFv-Fc.

5. The isolated antibody of claim 1, which has the amino acid sequence of SEQ ID NO: 13 or 14.

6. The isolated antibody of claim 1, which is conjugated with a marker selected from the group consisting of an enzyme, a fluorescent material and a radioactive material.

7. A composition comprising the antibody of claim 1 as an active ingredient.

8. The composition of claim 7, wherein the antibody is a whole antibody selected from the group consisting of IgG, IgM, IgA, IgD and IgE.

9. The composition of claim 7, wherein the antibody is an antibody fragment selected from the group consisting of scFv, (scFv)$_2$, Fab, Fab', F(ab')$_2$ and scFv-Fc.

10. The composition of claim 7, wherein the antibody has the amino acid sequence of SEQ ID NO: 13 or 14.

* * * * *

SEQUENCE LISTING

```
<160> NUMBER OF SEQ ID NOS: 22

<210> SEQ ID NO 1
<211> LENGTH: 10
<212> TYPE: PRT
<213> ORGANISM: Artificial
<220> FEATURE:
<223> OTHER INFORMATION: Synthetic construct

<400> SEQUENCE: 1

Gly Asp Ser Val Ser Ser Thr Thr Val Ala
 1               5                  10

<210> SEQ ID NO 2
<211> LENGTH: 10
<212> TYPE: PRT
<213> ORGANISM: Artificial
<220> FEATURE:
<223> OTHER INFORMATION: Synthetic construct

<400> SEQUENCE: 2

Thr Tyr Tyr Arg Ser Lys Trp Tyr Asn Glu
 1               5                  10

<210> SEQ ID NO 3
<211> LENGTH: 12
<212> TYPE: PRT
<213> ORGANISM: Artificial
<220> FEATURE:
<223> OTHER INFORMATION: Synthetic construct

<400> SEQUENCE: 3

Arg Glu Pro Asp Ala Gly Arg Gly Ala Phe Asp Ile
 1               5                  10

<210> SEQ ID NO 4
<211> LENGTH: 7
<212> TYPE: PRT
<213> ORGANISM: Artificial
```

```
<220> FEATURE:
<223> OTHER INFORMATION: Synthetic construct

<400> SEQUENCE: 4

Gln Ser Val Ser Ser His
 1               5

<210> SEQ ID NO 5
<211> LENGTH: 18
<212> TYPE: PRT
<213> ORGANISM: Artificial
<220> FEATURE:
<223> OTHER INFORMATION: Synthetic construct

<400> SEQUENCE: 5

Gly Ala Ser Ser Arg Ala Thr Gly Ile Pro Asp Arg Phe Ser Gly Ser
 1               5                  10                  15

Gly Ser

<210> SEQ ID NO 6
<211> LENGTH: 11
<212> TYPE: PRT
<213> ORGANISM: Artificial
<220> FEATURE:
<223> OTHER INFORMATION: Synthetic construct

<400> SEQUENCE: 6

Gln Gln Arg Ser Asn Trp Pro Pro Arg Ala Val
 1               5                  10

<210> SEQ ID NO 7
<211> LENGTH: 10
<212> TYPE: PRT
<213> ORGANISM: Artificial
<220> FEATURE:
<223> OTHER INFORMATION: Synthetic construct

<400> SEQUENCE: 7

Gly Asp Ser Val Ser Asn Asn Asn Ala Ala
 1               5                  10

<210> SEQ ID NO 8
<211> LENGTH: 9
<212> TYPE: PRT
<213> ORGANISM: Artificial
<220> FEATURE:
<223> OTHER INFORMATION: Synthetic construct

<400> SEQUENCE: 8

Thr Tyr Tyr Arg Ser Lys Trp Tyr Asn
 1               5

<210> SEQ ID NO 9
<211> LENGTH: 11
<212> TYPE: PRT
<213> ORGANISM: Artificial
<220> FEATURE:
<223> OTHER INFORMATION: Synthetic construct

<400> SEQUENCE: 9

Arg Arg Gly Asp Gly Asn Ser Tyr Phe Asp Tyr
 1               5                  10

<210> SEQ ID NO 10
<211> LENGTH: 7
<212> TYPE: PRT
<213> ORGANISM: Artificial
```

```
<220> FEATURE:
<223> OTHER INFORMATION: Synthetic construct

<400> SEQUENCE: 10

Gln Ser Val Ser Ser Gly Tyr
 1               5

<210> SEQ ID NO 11
<211> LENGTH: 16
<212> TYPE: PRT
<213> ORGANISM: Artificial
<220> FEATURE:
<223> OTHER INFORMATION: Synthetic construct

<400> SEQUENCE: 11

Gly Ala Ser Thr Arg Ala Thr Gly Ile Pro Asp Arg Phe Ser Gly Ser
 1               5                  10                  15

<210> SEQ ID NO 12
<211> LENGTH: 9
<212> TYPE: PRT
<213> ORGANISM: Artificial
<220> FEATURE:
<223> OTHER INFORMATION: Synthetic construct

<400> SEQUENCE: 12

His Gln Tyr Gly Ser Ser Pro Asn Thr
 1               5

<210> SEQ ID NO 13
<211> LENGTH: 248
<212> TYPE: PRT
<213> ORGANISM: Artificial
<220> FEATURE:
<223> OTHER INFORMATION: Synthetic construct

<400> SEQUENCE: 13

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Thr
                20                  25                  30

Thr Val Ala Trp Asp Trp Ile Arg Gln Ser Pro Ser Arg Gly Leu Glu
            35                  40                  45

Trp Leu Gly Arg Thr Tyr Tyr Arg Ser Lys Trp Tyr Asn Glu Tyr Ala
        50                  55                  60

Val Ser Val Lys Ser Arg Ile Thr Ile Asn Val Asp Thr Ser Lys Asn
 65                  70                  75                  80

Gln Ile Ser Leu Gln Leu Asn Ser Val Thr Pro Glu Asp Thr Ala Val
                85                  90                  95

Tyr Tyr Cys Ala Arg Glu Pro Asp Ala Gly Arg Gly Ala Phe Asp Ile
            100                 105                 110

Trp Gly Gln Gly Thr Thr Val Ser Pro Leu Arg Trp Gly Arg Phe
        115                 120                 125

Gly Trp Arg Gly Leu Gly Arg Gly Trp Leu Arg Ser Pro Val Thr Gln
        130                 135                 140

Ser Pro Gly Thr Leu Ser Leu Ser Pro Gly Glu Arg Ala Thr Leu Ser
145                 150                 155                 160

Cys Arg Ala Ser Gln Ser Val Ser Ser His Leu Ala Trp Tyr Gln
            165                 170                 175

Gln Lys Pro Gly Gln Ala Pro Arg Leu Leu Ile Tyr Gly Ala Ser Ser
            180                 185                 190
```

Arg Ala Thr Gly Ile Pro Asp Arg Phe Ser Gly Ser Gly Ser Gly Thr
        195                 200                 205

Asp Phe Thr Leu Thr Ile Ser Ser Leu Glu Pro Glu Asp Phe Ala Val
    210                 215                 220

Tyr Tyr Cys Gln Gln Arg Ser Asn Trp Pro Pro Arg Ala Val Phe Gly
225                 230                 235                 240

Gln Gly Thr Arg Leu Glu Ile Lys
            245

<210> SEQ ID NO 14
<211> LENGTH: 248
<212> TYPE: PRT
<213> ORGANISM: Artificial
<220> FEATURE:
<223> OTHER INFORMATION: Synthetic construct

<400> SEQUENCE: 14

Gln Val Gln Leu Gln Gln Ser Gly Pro Gly Arg Val Gln Pro Ser Gln
 1               5                  10                  15

Thr Leu Ser Leu Thr Cys Ala Ile Ser Gly Asp Ser Val Ser Asn Asn
            20                  25                  30

Asn Ala Ala Trp Tyr Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ser Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Gly Asp Gly Asn Ser Tyr Phe Asp Tyr Trp
            100                 105                 110

Gly Gln Gly Thr Leu Val Thr Val Ser Ser Gly Ile Leu Arg Trp Gly
        115                 120                 125

Arg Phe Gly Trp Arg Gly Leu Gly Arg Gly Trp Leu Glu Ile Val Leu
    130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Gly Tyr Val Ser Trp
                165                 170                 175

Tyr Arg Gln Lys Pro Gly Gln Ala Pro Arg Leu Leu Ile Tyr Gly Ala
            180                 185                 190

Ser Thr Arg Ala Thr Gly Ile Pro Asp Arg Phe Ser Gly Ser Gly Ser
        195                 200                 205

Gly Thr Asp Phe Thr Leu Thr Ile Ser Arg Leu Glu Pro Glu Asp Phe
    210                 215                 220

Ala Val Tyr Tyr Cys His Gln Tyr Gly Ser Ser Pro Asn Thr Tyr Gly
225                 230                 235                 240

Gln Gly Thr Lys Val Gly Ile Lys
            245

<210> SEQ ID NO 15
<211> LENGTH: 744
<212> TYPE: DNA
<213> ORGANISM: Artificial
<220> FEATURE:
<223> OTHER INFORMATION: Synthetic construct

<400> SEQUENCE: 15

```
caggtacagc tgcagcagtc aggtccagga ctggtgaagc cctcgcagac cctctcactc      60
acctgtgcca tctccgggga cagtgtctct agcaccactg ttgcctggga ctggatcagg     120
cagtccccat cgagaggcct tgagtggctg ggaaggacat attataggtc gaagtggtat     180
aatgaatatg cagtatctgt gaaaagtcga ataaccatca atgtagacac atccaagaac     240
cagatctccc tgcagctgaa ctctgtgact cccgaggaca cggccgtcta ttactgtgca     300
agagagccag atgccggcag gggggctttt gatatctggg gccaaggac cacggtcacc      360 tctcctctga ggtgggggcg gttcgggtgg cgggggctcg ggcgggggtg gctcagatct     420
ccagttaccc agtctccagg caccctgtct ttgtctccag gggaaagagc caccctctcc     480
tgcagggcca gtcagagtgt tagcagcagc cacttagcct ggtaccagca gaaacctggc     540
caggctccca ggctcctcat ctatggtgca tccagcaggg ccactggcat cccagacagg     600
ttcagtggca gtgggtctgg gacagacttc actctcacca tcagcagcct agagcctgaa     660
gattttgcag tttattactg tcagcagcgt agcaactggc ctccgcgggc ggtcttcggc     720
caagggacac gactggagat taaa                                            744

<210> SEQ ID NO 16
<211> LENGTH: 744
<212> TYPE: DNA
<213> ORGANISM: Artificial
<220> FEATURE:
<223> OTHER INFORMATION: Synthetic construct

<400> SEQUENCE: 16
caggtacagc tgcagcagtc aggtccagga cgggtgcagc cctcgcagac cctctcactc      60
acctgtgcca tctccgggga cagtgtctct aacaacaatg ctgcttggta ctggatcagg     120
cagtccccat cgagaggcct tgagtggctg ggaaggacat actacaggtc caagtggtat     180
aatgattatg cagtatctgt gaaaagtcga ataaccatca gcccagacac gtccaagaac     240
cagttctccc tgcagttgaa ctctgtgact cccgaggaca cggctgtgta ttactgtgca     300
agaagaggag atgggaactc ctactttgac tactggggcc agggaaccct ggtcaccgtc     360
tcctcaggaa ttctaaggtg ggggcggttc gggtggcggg ggctcgggcg ggggtggctc     420
gaaattgtat tgacacagtc tccaggcacc ctgtctttgt ctccagggga aagagccacc     480
ctctcctgca gggccagtca gagtgttagc agcggctacg tatcctggta ccggcagaaa     540
cctggccagg ctccccggct cctcatctat ggtgcatcca ccagggccac tggcatccca     600
gacaggttca gtggcagtgg gtctgggaca gacttcactc tcaccatcag cagactggag     660
cctgaagatt ttgcagtgta ttactgtcac cagtatggta gctcacccaa cacttatggc     720
caggggacca aggtggggat caaa                                            744

<210> SEQ ID NO 17
<211> LENGTH: 33
<212> TYPE: DNA
<213> ORGANISM: Artificial
<220> FEATURE:
<223> OTHER INFORMATION: Synthetic construct

<400> SEQUENCE: 17 cgagccccg ccacccgaac cgcccccacc tct                                    33

<210> SEQ ID NO 18
<211> LENGTH: 41
<212> TYPE: DNA
<213> ORGANISM: Artificial
<220> FEATURE:
```

-continued

```
<223> OTHER INFORMATION: Synthetic construct

<400> SEQUENCE: 18
ggttcgggtg gcgggggctc gggcgggggt ggctcagatc t                41

<210> SEQ ID NO 19
<211> LENGTH: 54
<212> TYPE: DNA
<213> ORGANISM: Artificial
<220> FEATURE:
<223> OTHER INFORMATION: Synthetic construct

<400> SEQUENCE: 19
agtggtggtg gtggttctgg tggtggtggt tctggtggtg gtggttctgc tagc      54

<210> SEQ ID NO 20
<211> LENGTH: 54
<212> TYPE: DNA
<213> ORGANISM: Artificial
<220> FEATURE:
<223> OTHER INFORMATION: Synthetic construct

<400> SEQUENCE: 20
tcagatctcg agctattaca agtcctcttc agaaataagc ttttgttcgg atcc      54

<210> SEQ ID NO 21
<211> LENGTH: 22
<212> TYPE: DNA
<213> ORGANISM: Artificial
<220> FEATURE:
<223> OTHER INFORMATION: Synthetic construct

<400> SEQUENCE: 21
gttccagact acgctctgca gg                                     22

<210> SEQ ID NO 22
<211> LENGTH: 24
<212> TYPE: DNA
<213> ORGANISM: Artificial
<220> FEATURE:
<223> OTHER INFORMATION: Synthetic construct

<400> SEQUENCE: 22
gattttgtta catctacact gttg                                   24
```